US007604950B2

(12) United States Patent
Mathialagan et al.

(10) Patent No.: US 7,604,950 B2
(45) Date of Patent: Oct. 20, 2009

(54) METHODS FOR EARLY DETECTION OF PREGNANCY IN COWS

(75) Inventors: Nagappan Mathialagan, Ballwin, MO (US); Michael McGrath, Chesterfield, MO (US); Robert Schenkel, St. Louis, MO (US)

(73) Assignee: Monsanto Technology LLC, St. Louis, MO (US)

( * ) Notice: Subject to any disclaimer, the term of this patent is extended or adjusted under 35 U.S.C. 154(b) by 87 days.

(21) Appl. No.: 11/587,391

(22) PCT Filed: Apr. 27, 2005

(86) PCT No.: PCT/US2005/014458

§ 371 (c)(1),
(2), (4) Date: Oct. 24, 2006

(87) PCT Pub. No.: WO2006/073447

PCT Pub. Date: Jul. 13, 2006

(65) Prior Publication Data

US 2008/0003695 A1    Jan. 3, 2008

Related U.S. Application Data

(60) Provisional application No. 60/566,282, filed on Apr. 29, 2004.

(51) Int. Cl.
*G01N 33/53* (2006.01)
(52) U.S. Cl. ............................ 435/7.1; 435/4; 435/7.92; 424/438; 424/811; 514/2
(58) Field of Classification Search ........................ None
See application file for complete search history.

(56) References Cited

U.S. PATENT DOCUMENTS 5,455,009 A * 10/1995 Vogler et al. ................. 422/102
2003/0073248 A1 * 4/2003 Roth et al. ................... 436/510
2007/0184558 A1   8/2007 Roth et al. ................... 436/510

FOREIGN PATENT DOCUMENTS

WO    WO 99/47934    9/1999
WO    WO 03/043524   5/2003

OTHER PUBLICATIONS

Gonzalez et al., Theriogenology, 1999, 52:717-725.*
Ishiwata H et al. (2003), Characterization of gene expression profiles in early bovine pregnancy using a custom cDNA microarray, *Molecular Reproduction and Development* 65:9-18.
Jonathan A. Green et al., "The Establishment of an ELISA for the Detection of Pregnancy-Associated Glycoproteins (PAGs) in the Serum of Pregnant Cows and Heifers", *Theriogenology*, 63:1481-1503 (2005).
Osman V. Patel et al., "Quantitative Analysis Throughout Pregnancy of Placentomal and Interplacentomal Expression of Pregnancy-Associated Glycoproteins-1 and -9 in the Cow", *Molecular Reproduction and Development*, 67:257-263 (2004).
Austin L. Hughes et al., "Adaptive Diversification Within a Large Family of Recently Duplicated, Placentally Expressed Genes", *PNAS*, 97(7):3319-3323 (2000).
Jonathan A. Green et al., "Pregnancy-Associated Bovine and Ovine Glycoproteins Exhibit Spatially and Temporally Distinct Expression Patterns During Pregnancy", *Biology of Reproduction*, 62:1624-1631 (2000).
Fan Huang et al., "Isolation, Purification, and Characterization of Pregnancy-Specific Protein B from Elk and Moose Placenta", *Biology of Reproduction*, 61:1056-1061 (1999).
Jonathan A. Green et al., "Identification of a New Aspartic Proteinase Expressed by the Outer Chorionic Cell Layer of the Equine Placenta", *Biology of Reproduction*, 60:1069-1077 (1999).
O. Szenci et al., "Comparison of Ultrasonography, Bovine Pregnancy-Specific Protein B, and Bovine Pregnancy-Associated Glycoprotein 1 Tests for Pregnancy Detection in Dairy Cows", *Theriogenology* 50:77-88 (1998).
Sancai Xie et al., "The Diversity and Evolutionary Relationships of the Pregnancy-Associated Glycoproteins, an Aspartic Proteinase Subfamily Consisting of Many Trophoblast-Expressed Genes", *Proc. Natl. Acad. Sci.*, 94:12809-12816 (1997).
Nagappan Mathialagan et al., "Pepsin-Inhibitory Activity of the Uterine Serpins," *Proc. Natl. Acad. Sci.*, 93:13653-13658 (1996).
G.H. Kiracofe et al., "Pregnancy-Specific Protein B in Serum of Postpartum Beef Cows", *J. Anim. Sci.*, 71:2199-2205 (1993).

(Continued)

*Primary Examiner*—Michael Szperka
(74) *Attorney, Agent, or Firm*—Matthew L. Madsen; Howrey LLP

(57) ABSTRACT

Disclosed are methods for determining the pregnancy status of a cow by detecting a pregnancy-associated glycoprotein (PAG) level that comprises proteins present in an acidic protein fraction of day 55 to day 60 bovine placental tissue. These methods may involve using novel polyclonal and monoclonal antibodies that have been generated using the acidic protein fraction as an immunogen. According to the method, the cow is pregnant when the PAG level is present at an elevated level in a sample obtained from the cow. The invention provides accurate methods of detecting pregnancy at early stages and has the benefit of allowing early post partum detection of pregnancy status with few false positive results. The antibodies for detecting the PAG level will also be useful in combination with detecting elevated progesterone levels, thus providing an even more effective pregnancy detection method. The benefit of this early pregnancy detection is that identifying cows that are not pregnant very shortly after breeding allows for timely rebreeding and minimizes the amount of time the cow is open. Also disclosed are methods for making a breeding decision for a cow. These methods allow a herd manager to make breeding decisions based on the PAG level and optionally, progesterone levels, detected in a biological sample taken from a cow suspected of being in the early stages of pregnancy.

38 Claims, 12 Drawing Sheets

OTHER PUBLICATIONS

Sancai Xie et al., "Identification of the Major Pregnancy-Specific Antigens of Cattle and Sheep as Inactive Members of the Aspartic Proteinase Family", *Proc. Natl. Acad Sci.*, 88:10247-10251 (1991).

Andre Pagnah Zoli et al., "Purification and Characterization of a Bovine Pregnancy-Associated Glycoprotein", *Biology of Reproduction*, 45:1-10 (1991).

* cited by examiner

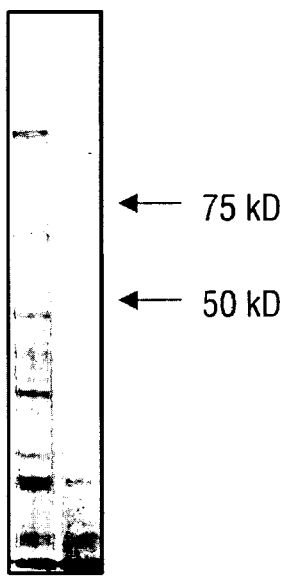 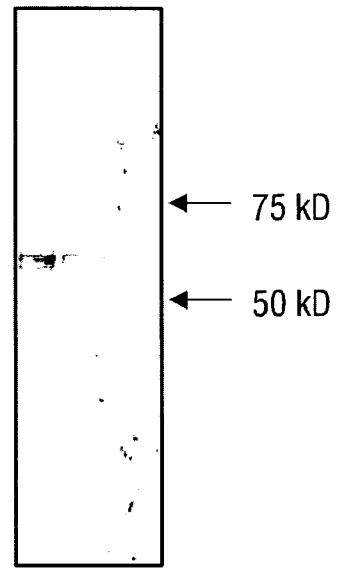
*FIG. 5A*      *FIG. 5B*
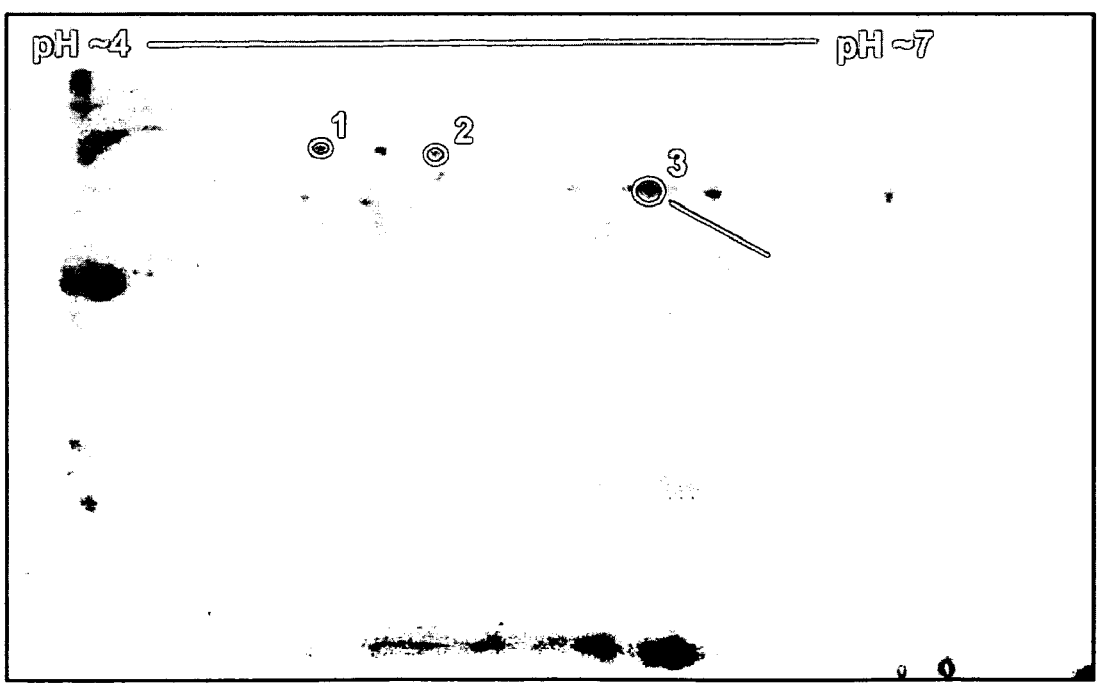
*FIG. 6*

SEQ ID NO:1
>gi|28314331|gb|BP112041.1|BP112041 BP112041 ORCS bovine utero-placenta cDNA Bos taurus cDNA clone ORCS12646 5', mRNA sequence GGCACGAGGCACCAGTCCAGCCTGTTCTACACACGTTAGGTTCAGACATCTTCAGTCTTCCACCTTCCGAC
CTACCAATAAGACCTTCAGGATCACCTATGGATCTGGGAGAATGAAAGGAGTTGTTGCTCATGACACAGTTC
GGATCGGGGACCTTGTAAGCACTGACCAGCCGTTTGGTCTGTAAGCACGGCAGAATACGGGTTTAAGGATATG
CCTTTTGATGGTGTCTTGGGCTTGAACTACCCCAACATATCCTCTCTGGAGCAATCCCATCTTTGACAAG
CTGAAGAATCAAGGTGCCATTTCTGAGCCTGTTTTTGCCTTCTACTTCAGCAAGACAAGCGGGAGGGCAG
TGTGGTGATGTTTGGTGGGGTGGACCACCGCTACTACAAGGGAGAGCTCAAGTGGGTACCATTGATCCAA
GCGGGTG SEQ ID NO:2
>MonPAG/EST BP112041 Predicted Amino acid sequence ARGTSPACSTHVRFRHLQSSTFRPTNKTFRITYGSSGRMKGVVAHDTVRIGDLVSTDQPFGLSTAEYGFKDMPF
DGVLGLNYPNISSSGAIPIFDKLKNQGAISEPVFAFYFSKDKREGSVVMFGGVDHRYYKGELKWVPLIQAGX

FIG. 7

Bos Taurus (NM176617) Pregnancy-associated glycoprotein 6
Spots 1 & 2

| Mz | Charge | Mr(calc) | Start | End | Score | Peptide sequence |
|---|---|---|---|---|---|---|
| 853.4334 | 2 | 1686.8651 | 147 | 162 | 94.87% | IGDLVSTDQPFGLCLK (SEQ ID NO:3) |
| 615.2964 | 2 | 1210.6022 | 183 | 193 | 95.45% | TFSGAFPIFDK (SEQ ID NO:4) |
| 886.4468 | 2 | 1752.8722 | 196 | 211 | 98.95% | NEGAISEPVFAFYLSK (SEQ ID NO:5) |
| 592.9523 | 3 | 1757.8154 | 212 | 227 | 89.57% | DKQEGSVVMFGGVDHR (SEQ ID NO:6) |
| 767.3938 | 3 | 2281.1953 | 266 | 287 | 90.78% | ALVDTGTSDIVGPSTLVNNIWK (SEQ ID NO:7) |
| 467.2134 | 2 | 914.4286 | 362 | 368 | 99% | YFSVFDR (SEQ ID NO:8) |

Spot 3
Bos Taurus (NM176626) Pregnancy-associated glycoprotein 18

| Mz | Charge | Mr(calc) | Start | End | Score | Peptide sequence |
|---|---|---|---|---|---|---|
| 885.67 | 2 | 1751.89 | 197 | 212 | 99% | NQGAISEPVFAFYLSK (SEQ ID NO:9) |
| 707.66 | 2 | 1395.74 | 267 | 280 | 99% | AVVDTGTSLIEGPR (SEQ ID NO:10) |
| 545.22 | 2 | 1070.53 | 363 | 370 | 99% | RYFSVFDR (SEQ ID NO:11) |

*FIG. 8A*

Bos Taurus (NM176615) Pregnancy-associated glycoprotein 4

| Mz | Charge | Mr(calc) | Start | End | Score | Peptide sequence |
|---|---|---|---|---|---|---|
| 544.6 | 2 | 1069.52 | 127 | 136 | 83.18% | TFSITYGSGR (SEQ ID NO:12) |
| 494.64 | 2 | 969.56 | 323 | 331 | 98.56% | VPGQAYILK (SEQ ID NO:13) |
| 467.08 | 2 | 914.43 | 363 | 369 | 97.29% | YFSVFDR (SEQ ID NO:14) |

Bos Taurus Pregnancy-associated glycoprotein (Mon PAG)|BP112401 (bovineEST)

| Mz | Charge | Mr(calc) | Start | End | Score | Peptide sequence |
|---|---|---|---|---|---|---|
| 617.77 | 2 | 1215.65 | 183 | 194 | 99% | ISSSGAIPIFDK (SEQ ID NO:15) |
| 695.12 | 2 | 1370.64 | 213 | 225 | 85.46% | EGSVVMFGGVDHR (SEQ ID NO:16) |
| 902.9173 | 2 | 1785.0665 | 196 | 211 | 99% | NQGAISEPVFAFYFSK (SEQ ID NO:17) |
| 1135.79 | 2 | 2245.46 | 147 | 167 | 98% | IGDLVSTDQPFGLSTAEYGFK (SEQ ID NO:18) |

FIG. 8B

Bos Taurus (AAF05999) Pregnancy-associated glycoprotein 16

| Mz | Charge | Mr(calc) | Start | End | Score | Peptide sequence |
|---|---|---|---|---|---|---|
| 926.5 | 2 | 1853.1 | 178 | 194 | 99% | LNYPNLSCSGAIPIFDK (SEQ ID NO:19) |
| 695.12 | 2 | 1370.64 | 216 | 228 | 86.00% | EGSVVMFGGVDHR (SEQ ID NO:20) |
| 598.2 | 2 | 1196.41 | 232 | 241 | 89% | GELNWVPLIR (SEQ ID NO:21) |
| 467.08 | 2 | 914.43 | 363 | 369 | 97.29% | YFSVFDR (SEQ ID NO:22) |

Bos Taurus (AAF06002) Pregnancy-associated glycoprotein 19

| Mz | Charge | Mr(calc) | Start | End | Score | Peptide sequence |
|---|---|---|---|---|---|---|
| 544.6 | 2 | 1069.52 | 127 | 136 | 83.18% | TFSITYGSGR (SEQ ID NO:23) |
| 885.67 | 2 | 1751.89 | 197 | 212 | 99% | NQGAISEPVFAFYLSK (SEQ ID NO:24) |
| 695.12 | 2 | 1370.64 | 216 | 228 | 86.00% | EGSVVMFGGVDHR (SEQ ID NO:25) |
| 467.08 | 2 | 914.43 | 363 | 369 | 97.29% | YFSVFDR (SEQ ID NO:26) |

Bos Taurus (NM_176620) Pregnancy-associated glycoprotein 9

| Mz | Charge | Mr(calc) | Start | End | Score | Peptide sequence |
|---|---|---|---|---|---|---|
| 885.67 | 2 | 1751.89 | 197 | 212 | 99% | NQGAISEPVFAFYLSK (SEQ ID NO:27) |
| 545.22 | 2 | 1070.5 | 361 | 368 | 99% | RYFSVFDR (SEQ ID NO:28) |

FIG. 8C

SEQUENCE LISTING

<160> NUMBER OF SEQ ID NOS: 28

<210> SEQ ID NO 1
<211> LENGTH: 434
<212> TYPE: DNA
<213> ORGANISM: Bos taurus
<220> FEATURE:
<221> NAME/KEY: misc_feature
<222> LOCATION: (1)..(434)
<223> OTHER INFORMATION: BP112041; EST of ORCS  bovine utero-placenta
      cDNA Bos taurus cDNA

<400> SEQUENCE: 1
ggcacgaggc accagtccag cctgttctac acacgttagg ttcagacatc ttcagtcttc      60
caccttccga cctaccaata agaccttcag gatcacctat ggatctggga gaatgaaagg     120
agttgttgct catgacacag ttcggatcgg ggaccttgta agcactgacc agccgtttgg     180
tctaagcacg gcagaatacg ggtttaagga tatgcctttt gatggtgtct tgggcttgaa     240
ctaccccaac atatcctctt ctggagcaat ccccatcttt gacaagctga gaatcaagg     300 tgccatttct gagcctgttt ttgccttcta cttcagcaaa gacaagcggg agggcagtgt     360
ggtgatgttt ggtggggtgg accaccgcta ctacaaggga gagctcaagt gggtaccatt     420
gatccaagcg ggtg                                                      434

<210> SEQ ID NO 2
<211> LENGTH: 145
<212> TYPE: PRT
<213> ORGANISM: Bos taurus
<220> FEATURE:
<221> NAME/KEY: MISC_FEATURE
<222> LOCATION: (1)..(145)
<223> OTHER INFORMATION: Predicted amino acid sequence
<220> FEATURE:
<221> NAME/KEY: MISC_FEATURE
<222> LOCATION: (145)..(145)
<223> OTHER INFORMATION: xaa can be any naturally occuring amino acid

<400> SEQUENCE: 2

Ala Arg Gly Thr Ser Pro Ala Cys Ser Thr His Val Arg Phe Arg His
1               5                   10                  15

Leu Gln Ser Ser Thr Phe Arg Pro Thr Asn Lys Thr Phe Arg Ile Thr
            20                  25                  30

Tyr Gly Ser Gly Arg Met Lys Gly Val Val Ala His Asp Thr Val Arg
        35                  40                  45

Ile Gly Asp Leu Val Ser Thr Asp Gln Pro Phe Gly Leu Ser Thr Ala
    50                  55                  60

Glu Tyr Gly Phe Lys Asp Met Pro Phe Asp Gly Val Leu Gly Leu Asn
65                  70                  75                  80

Tyr Pro Asn Ile Ser Ser Ser Gly Ala Ile Pro Ile Phe Asp Lys Leu
                85                  90                  95

Lys Asn Gln Gly Ala Ile Ser Glu Pro Val Phe Ala Phe Tyr Phe Ser
            100                 105                 110

Lys Asp Lys Arg Glu Gly Ser Val Val Met Phe Gly Val Asp His
            115                 120                 125

Arg Tyr Tyr Lys Gly Glu Leu Lys Trp Val Pro Leu Ile Gln Ala Gly
        130                 135                 140

Xaa
145

```
<210> SEQ ID NO 3
<211> LENGTH: 16
<212> TYPE: PRT
<213> ORGANISM: Bos taurus
<220> FEATURE:
<221> NAME/KEY: MISC_FEATURE
<222> LOCATION: (1)..(16)
<223> OTHER INFORMATION: Partial amino acid sequence from spots 1 & 2;
      PAG 6

<400> SEQUENCE: 3

Ile Gly Asp Leu Val Ser Thr Asp Gln Pro Phe Gly Leu Cys Leu Lys
1               5                   10                  15

<210> SEQ ID NO 4
<211> LENGTH: 11
<212> TYPE: PRT
<213> ORGANISM: Bos taurus
<220> FEATURE:
<221> NAME/KEY: MISC_FEATURE
<222> LOCATION: (1)..(11)
<223> OTHER INFORMATION: Partial amino acid sequence from spots 1 & 2;
      PAG 6

<400> SEQUENCE: 4

Thr Phe Ser Gly Ala Phe Pro Ile Phe Asp Lys
1               5                   10

<210> SEQ ID NO 5
<211> LENGTH: 16
<212> TYPE: PRT
<213> ORGANISM: Bos taurus
<220> FEATURE:
<221> NAME/KEY: MISC_FEATURE
<222> LOCATION: (1)..(16)
<223> OTHER INFORMATION: Partial amino acid sequence from spots 1 & 2;
      PAG 6

<400> SEQUENCE: 5

Asn Glu Gly Ala Ile Ser Glu Pro Val Phe Ala Phe Tyr Leu Ser Lys
1               5                   10                  15

<210> SEQ ID NO 6
<211> LENGTH: 16
<212> TYPE: PRT
<213> ORGANISM: Bos taurus
<220> FEATURE:
<221> NAME/KEY: MISC_FEATURE
<222> LOCATION: (1)..(16)
<223> OTHER INFORMATION: Partial amino acid sequence from spots 1 & 2;
      PAG 6

<400> SEQUENCE: 6

Asp Lys Gln Glu Gly Ser Val Val Met Phe Gly Gly Val Asp His Arg
1               5                   10                  15

<210> SEQ ID NO 7
<211> LENGTH: 22
<212> TYPE: PRT
<213> ORGANISM: Bos taurus
<220> FEATURE:
<221> NAME/KEY: MISC_FEATURE
<222> LOCATION: (1)..(22)
<223> OTHER INFORMATION: Partial amino acid sequence from spots 1 & 2;
      PAG 6

<400> SEQUENCE: 7

Ala Leu Val Asp Thr Gly Thr Ser Asp Ile Val Gly Pro Ser Thr Leu
1               5                   10                  15
```

```
Val Asn Asn Ile Trp Lys
            20

<210> SEQ ID NO 8
<211> LENGTH: 7
<212> TYPE: PRT
<213> ORGANISM: Bos taurus
<220> FEATURE:
<221> NAME/KEY: MISC_FEATURE
<222> LOCATION: (1)..(7)
<223> OTHER INFORMATION: Partial amino acid sequence from spots 1 & 2;
      PAG 6

<400> SEQUENCE: 8

Tyr Phe Ser Val Phe Asp Arg
1               5

<210> SEQ ID NO 9
<211> LENGTH: 16
<212> TYPE: PRT
<213> ORGANISM: Bos taurus
<220> FEATURE:
<221> NAME/KEY: MISC_FEATURE
<222> LOCATION: (1)..(16)
<223> OTHER INFORMATION: Partial amino acid sequence from spot 3; PAG 18

<400> SEQUENCE: 9

Asn Gln Gly Ala Ile Ser Glu Pro Val Phe Ala Phe Tyr Leu Ser Lys
1               5                   10                  15

<210> SEQ ID NO 10
<211> LENGTH: 14
<212> TYPE: PRT
<213> ORGANISM: Bos taurus
<220> FEATURE:
<221> NAME/KEY: MISC_FEATURE
<222> LOCATION: (1)..(14)
<223> OTHER INFORMATION: Partial amino acid sequence from spot 3; PAG 18

<400> SEQUENCE: 10

Ala Val Val Asp Thr Gly Thr Ser Leu Ile Glu Gly Pro Arg
1               5                   10

<210> SEQ ID NO 11
<211> LENGTH: 8
<212> TYPE: PRT
<213> ORGANISM: Bos taurus
<220> FEATURE:
<221> NAME/KEY: MISC_FEATURE
<222> LOCATION: (1)..(8)
<223> OTHER INFORMATION: Partial amino acid sequence from spot 3; PAG 18

<400> SEQUENCE: 11

Arg Tyr Phe Ser Val Phe Asp Arg
1               5

<210> SEQ ID NO 12
<211> LENGTH: 10
<212> TYPE: PRT
<213> ORGANISM: Bos taurus
<220> FEATURE:
<221> NAME/KEY: MISC_FEATURE
<222> LOCATION: (1)..(10)
<223> OTHER INFORMATION: Partial amino acid sequence from spot 3; PAG 4

<400> SEQUENCE: 12

Thr Phe Ser Ile Thr Tyr Gly Ser Gly Arg
1               5                   10
```

```
<210> SEQ ID NO 13
<211> LENGTH: 9
<212> TYPE: PRT
<213> ORGANISM: Bos taurus
<220> FEATURE:
<221> NAME/KEY: MISC_FEATURE
<222> LOCATION: (1)..(9)
<223> OTHER INFORMATION: Partial amino acid sequence from spot 3; PAG 4

<400> SEQUENCE: 13

Val Pro Gly Gln Ala Tyr Ile Leu Lys
1               5

<210> SEQ ID NO 14
<211> LENGTH: 7
<212> TYPE: PRT
<213> ORGANISM: Bos taurus
<220> FEATURE:
<221> NAME/KEY: MISC_FEATURE
<222> LOCATION: (1)..(7)
<223> OTHER INFORMATION: Partial amino acid sequence from spot 3; PAG 4

<400> SEQUENCE: 14

Tyr Phe Ser Val Phe Asp Arg
1               5

<210> SEQ ID NO 15
<211> LENGTH: 12
<212> TYPE: PRT
<213> ORGANISM: Bos taurus
<220> FEATURE:
<221> NAME/KEY: MISC_FEATURE
<222> LOCATION: (1)..(12)
<223> OTHER INFORMATION: Partial amino acid sequence from spot 3; Mon
      PAG

<400> SEQUENCE: 15

Ile Ser Ser Ser Gly Ala Ile Pro Ile Phe Asp Lys
1               5                   10

<210> SEQ ID NO 16
<211> LENGTH: 13
<212> TYPE: PRT
<213> ORGANISM: Bos taurus
<220> FEATURE:
<221> NAME/KEY: MISC_FEATURE
<222> LOCATION: (1)..(13)
<223> OTHER INFORMATION: Partial amino acid sequence from spot 3; Mon
      PAG

<400> SEQUENCE: 16

Glu Gly Ser Val Val Met Phe Gly Gly Val Asp His Arg
1               5                   10

<210> SEQ ID NO 17
<211> LENGTH: 16
<212> TYPE: PRT
<213> ORGANISM: Bos taurus
<220> FEATURE:
<221> NAME/KEY: MISC_FEATURE
<222> LOCATION: (1)..(16)
<223> OTHER INFORMATION: Partial amino acid sequence from spot 3; Mon
      PAG

<400> SEQUENCE: 17

Asn Gln Gly Ala Ile Ser Glu Pro Val Phe Ala Phe Tyr Phe Ser Lys
1               5                   10                  15
```

<210> SEQ ID NO 18
<211> LENGTH: 21
<212> TYPE: PRT
<213> ORGANISM: Bos taurus
<220> FEATURE:
<221> NAME/KEY: MISC_FEATURE
<222> LOCATION: (1)..(21)
<223> OTHER INFORMATION: Partial amino acid sequence from spot 3; Mon
      PAG

<400> SEQUENCE: 18

Ile Gly Asp Leu Val Ser Thr Asp Gln Pro Phe Gly Leu Ser Thr Ala
1               5                   10                  15

Glu Tyr Gly Phe Lys
            20

<210> SEQ ID NO 19
<211> LENGTH: 17
<212> TYPE: PRT
<213> ORGANISM: Bos taurus
<220> FEATURE:
<221> NAME/KEY: MISC_FEATURE
<222> LOCATION: (1)..(17)
<223> OTHER INFORMATION: Partial amino acid sequence from spot 3; PAG 16

<400> SEQUENCE: 19

Leu Asn Tyr Pro Asn Leu Ser Cys Ser Gly Ala Ile Pro Ile Phe Asp
1               5                   10                  15

Lys

<210> SEQ ID NO 20
<211> LENGTH: 13
<212> TYPE: PRT
<213> ORGANISM: Bos taurus
<220> FEATURE:
<221> NAME/KEY: MISC_FEATURE
<222> LOCATION: (1)..(13)
<223> OTHER INFORMATION: Partial amino acid sequence from spot 3; PAG 16

<400> SEQUENCE: 20

Glu Gly Ser Val Val Met Phe Gly Gly Val Asp His Arg
1               5                   10

<210> SEQ ID NO 21
<211> LENGTH: 10
<212> TYPE: PRT
<213> ORGANISM: Bos taurus
<220> FEATURE:
<221> NAME/KEY: MISC_FEATURE
<222> LOCATION: (1)..(10)
<223> OTHER INFORMATION: Partial amino acid sequence from spot 3; PAG 16

<400> SEQUENCE: 21

Gly Glu Leu Asn Trp Val Pro Leu Ile Arg
1               5                   10

<210> SEQ ID NO 22
<211> LENGTH: 7
<212> TYPE: PRT
<213> ORGANISM: Bos taurus
<220> FEATURE:
<221> NAME/KEY: MISC_FEATURE
<222> LOCATION: (1)..(7)
<223> OTHER INFORMATION: Partial amino acid sequence from spot 3; PAG 16

<400> SEQUENCE: 22

Tyr Phe Ser Val Phe Asp Arg

-continued

```
1               5

<210> SEQ ID NO 23
<211> LENGTH: 10
<212> TYPE: PRT
<213> ORGANISM: Bos taurus
<220> FEATURE:
<221> NAME/KEY: MISC_FEATURE
<222> LOCATION: (1)..(10)
<223> OTHER INFORMATION: Partial amino acid sequence from spot 3; PAG 19

<400> SEQUENCE: 23

Thr Phe Ser Ile Thr Tyr Gly Ser Gly Arg
1               5                   10

<210> SEQ ID NO 24
<211> LENGTH: 16
<212> TYPE: PRT
<213> ORGANISM: Bos taurus
<220> FEATURE:
<221> NAME/KEY: MISC_FEATURE
<222> LOCATION: (1)..(16)
<223> OTHER INFORMATION: Partial amino acid sequence from spot 3; PAG 19

<400> SEQUENCE: 24

Asn Gln Gly Ala Ile Ser Glu Pro Val Phe Ala Phe Tyr Leu Ser Lys
1               5                   10                  15

<210> SEQ ID NO 25
<211> LENGTH: 13
<212> TYPE: PRT
<213> ORGANISM: Bos taurus
<220> FEATURE:
<221> NAME/KEY: MISC_FEATURE
<222> LOCATION: (1)..(13)
<223> OTHER INFORMATION: Partial amino acid sequence from spot 3; PAG 19

<400> SEQUENCE: 25

Glu Gly Ser Val Val Met Phe Gly Gly Val Asp His Arg
1               5                   10

<210> SEQ ID NO 26
<211> LENGTH: 7
<212> TYPE: PRT
<213> ORGANISM: Bos taurus
<220> FEATURE:
<221> NAME/KEY: MISC_FEATURE
<222> LOCATION: (1)..(7)
<223> OTHER INFORMATION: Partial amino acid sequence from spot 3; PAG 19

<400> SEQUENCE: 26

Tyr Phe Ser Val Phe Asp Arg
1               5

<210> SEQ ID NO 27
<211> LENGTH: 16
<212> TYPE: PRT
<213> ORGANISM: Bos taurus
<220> FEATURE:
<221> NAME/KEY: MISC_FEATURE
<222> LOCATION: (1)..(16)
<223> OTHER INFORMATION: Partial amino acid sequence from spot 3; PAG 9

<400> SEQUENCE: 27

Asn Gln Gly Ala Ile Ser Glu Pro Val Phe Ala Phe Tyr Leu Ser Lys
1               5                   10                  15

<210> SEQ ID NO 28
```

```
-continued

<211> LENGTH: 8
<212> TYPE: PRT
<213> ORGANISM: Bos taurus
<220> FEATURE:
<221> NAME/KEY: MISC_FEATURE
<222> LOCATION: (1)..(8)
<223> OTHER INFORMATION: Partial amino acid sequence from spot 3; PAG 9

<400> SEQUENCE: 28

Arg Tyr Phe Ser Val Phe Asp Arg
1               5
```

METHODS FOR EARLY DETECTION OF PREGNANCY IN COWS

This Application is a §371 U.S. national phase application of International Application No. PCT/US2005/014458 filed Apr. 27, 2005, and claims the benefit of U.S. Provisional Application Ser. No. 60/566,282, filed Apr. 29, 2004, which is herein incorporated by reference.

BACKGROUND OF THE INVENTION

I. Field of the Invention

The present invention relates generally to the fields of veterinary medicine, reproductive biology and diagnostics. More specifically, the present invention relates to improved methods for accurate pregnancy detection in ungulates (hoofed animals), including ruminants such as bovines (e.g. dairy and beef cattle) and in ovines. The present invention also relates to antibodies, including polyclonal antibodies that have been generated using the PAG-55 enriched protein fraction as an immunogen.

II. Description of the Related Art

Pregnancy diagnosis is an important component in sound reproductive management, particularly in the dairy industry (Oltenacu et al., 1990), where a high proportion of artificial inseminations fail (Streenan and Diskin, 1986). A reliable yet simple pregnancy test for ruminants such as cattle has long been sought. Several procedures are available, including a milk progesterone assay (Oltenacu et al., 1990; Markusfeld et al., 1990), estrone sulfate analysis (Holdsworth et al., 1982; Warnick et al., 1995), rectal palpation (Hatzidakis et al., 1993), ultrasound (Beal et al., 1992; Cameron and Malmo, 1993), and blood tests for pregnancy-specific antigens. Of these, the progesterone milk assay is the most cost effective for the producer (Oltenacu et al., 1990; Markusfeld et al., 1990). Next best is rectal palpation, performed at day 50 post-insemination (Oltenacu et al., 1990).

Even though the prior procedures for pregnancy diagnosis are potentially useful, all have fallen short of expectations in terms of their practical, on-farm use. For example, measurements of milk or serum progesterone around day 18-22 yield unacceptably high rates of false positives (Oltenacu et al., 1990; Markusfeld et al., 1990). The presence of estrone sulfate in urine or serum provides another test, but is only useful after day 100 when concentrations rise (Holdsworth et al., 1982; Warnick et al., 1995).

The discovery of pregnancy-specific protein B (PSP-B) (Butler et al., 1982) provided a new approach to pregnancy diagnosis since it could be detected in the blood of pregnant cows by the fourth week of pregnancy (Sasser et al., 1986; Humblot et al., 1988). Two other groups have developed immunoassays that may be based on an identical or immunologically similar antigen (Zoli et al., 1992a; Mialon et al., 1993; Mialon et al., 1994). In one case, the antigen ($M_r$~67 kDa) was called bovine pregnancy-associated glycoprotein (boPAG; now boPAG-1) (Zoli et al., 1991, 1992a, 1992b); in the second, it was designated as pregnancy serum protein 60 (PSP60) (Mialon et al., 1993; Mialon et al., 1994). The term PAG refers generally to pregnancy associated glycoproteins, or pregnancy associated antigens. For a recent review of methods and a characterization of the current members of the boPAGs, see Green et al., *Theriogenology* 63:1481-1503 (2005), incorporated herein by reference in its entirety.

The immunoassay for PSP-B/boPAG1/PSP60 has several advantages. First, it can detect pregnancy relatively early. Second, interpretation of the assays does not require knowledge of the exact date of service, since boPAG-1 immunoreactive molecules are always present in the maternal serum of pregnant cows by day 28, and concentrations increase as pregnancy advances (Sasser et al., 1986; Mialon et al., 1993; Mialon et al., 1994).

There remain, however, two major disadvantages to this procedure. First, positive diagnosis in the fourth week of pregnancy remains somewhat uncertain because antigen concentrations in blood are low and somewhat variable. Second, boPAG1 concentrations rise markedly at term (Sasser et al., 1986; Zoli et al., 1992a; Mialon et al., 1993) and, due to the long circulating half-life of the molecule (Kiracofe et al., 1993), the antigen can still be detected 80-100 days postpartum (Zoli et al., 1992a; Mialon et al., 1993; Mialon et al., 1994; Kiracofe et al., 1993), compromising pregnancy diagnosis in cows bred within the early postpartum period. Thus, the test can be carried out in dairy cows at day 30 after artificial insemination (AI) only if the AI has been performed at 80 or more days post-partum.

There is a general need for easy, economic, sensitive, non-invasive, and accurate methods and tests for detecting pregnancy analytes in whole blood samples, especially ones that don't require any special equipment or chemicals. These methods would be particularly useful in field or rural settings where laboratory equipment, chemicals, and refrigerated storage are unavailable.

Specifically, there exists a need in the art for a pregnancy test that can be carried out reliably and early in pregnancy which could provide a definitive indication as to whether re-breeding or culling is required. In general, AI (artificial insemination) is successful less than 50% of the time in cattle and the producer must either rely on overt behavioral signals of return to estrus (that are easily missed) or delay re-breeding until pregnancy failure is confirmed by one of the methods described above. Such delays are extremely costly and constitute a major economic loss to the industry.

Specifically, there exists a need in the art for an accurate pregnancy test for ungulates that uses whole blood, which can be easily collected from the animal. Being able to use a whole blood sample with no special equipment or chemical treatment would facilitate reliable and early pregnancy detection allowing efficient action to be taken when re-breeding or culling is required.

Routine immunodetection pregnancy tests involve the detection of an analyte in blood serum. Prior methods for using serum from whole blood for this type of testing involved either additional physical components or matrices such as filters, glass fibers, bibulous agents, paper, fleece, cellulose, wool, asbestos fibers, or required single or multiple centrifugation steps, or required the addition of chemical agents, such as anti-red blood cell antibodies, poly lysine, or lectins.

Whole blood is easily obtained from mammals including farm animals; however, the separation of the interfering constituents such as red blood cells from the desired serum can be problematic in the field, including in farm settings. Thus, there is a need for an easy method that requires no additional filters, matrices, or centrifugation steps, and that allows using whole, clotted blood to detect any desired pregnancy analyte in the serum, using a variety of appropriate tests, such as immunodetection.

Consequently, there is a need for a feasible, economic, sensitive, non-invasive, and accurate pregnancy test for cattle, and other ruminants, that has low levels of false positive results and yet is sensitive enough to detect pregnancy (or more properly the absence thereof) early enough to allow a herd manager to identify non-pregnant ('open') cows for re-breeding.

SUMMARY OF THE INVENTION

The invention provides methods for the detection of pregnancy in an ungulate animal comprising: (a) obtaining a sample from said animal; (b) measuring the level of PAG-55 protein fraction in said sample; wherein an elevated level of PAG-55 protein fraction indicates that said animal is pregnant. This method may further comprise measuring the level of progesterone in the sample, and wherein elevated levels of PAG-55 protein fraction and progesterone indicate that said animal is pregnant. The sample may be from any suitable biological material, including saliva, serum, plasma, blood, milk or urine. In certain embodiments, the sample is a whole blood sample from an ungulate. In certain embodiments of the invention, the sample may be obtained from the animal at any day of gestation, including from about day 15 to day 30 post-insemination, including about day 15, 16, 17, 18, 19, 20, 21, 22, 23, 24, 25, 26, 27, 28, 29, 30 or later days of gestation. In certain embodiments of the invention, the animal is an ungulate (hoofed animals), including ruminants such as a bovine (including a beef or dairy cow), an ovine (such as sheep), or a caprine (such as a goat).

In additional embodiments of the invention, the method may further comprise: (i) allowing the whole blood to clot in the presence of a clot activator; (ii) allowing serum to extrude from the clotted whole blood without centrifugation; (iii) placing extruded serum in liquid communication with detection means comprising a reactant that is indicative of pregnancy; and (iv) determining whether at least one desired PAG-55 protein fraction antigen is present by reading the detection means. This method may include using clot activators that are selected from the group consisting of thrombin, phospholipids, kaolin, micronized silica, and calcium.

In one particular embodiment of the invention, the PAG-55 proteins that are analyzed are present in the maternal blood from about day 15 through the end of gestation.

Additional embodiments of the invention may include measuring the PAG-55 protein fraction wherein the PAG-55 protein fraction comprises at least one of the PAG antigens selected from the group consisting of PAG-4, PAG-6, PAG-9, PAG-16, PAG-18, PAG-19, and Mon PAG. Other embodiments may include measuring the PAG-55 protein fraction wherein the PAG-55 protein fraction comprises PAG-4, PAG-6, PAG-9, PAG-16, PAG-18, PAG-19, and Mon PAG.

The measuring of the present invention may comprise immunologic detection, including detecting the PAG-55 protein fraction levels with polyclonal antisera, polyclonal antibodies or fragments of polyclonal antibodies (Fab fragments). In another embodiment of the invention, the immunologic detection comprises detecting the PAG-55 protein fraction with a monoclonal antibody preparation.

Immunologic detection of the present invention may be carried out using any technique, including ELISA, RIA, lateral flow technology (such as test strips or dip sticks) and Western blot. The ELISA may comprise a sandwich ELISA comprising forming an immunocomplex between the PAG-55 protein fraction and a first antibody preparation fixed to a substrate and binding a second antibody preparation labeled with an enzyme to the immunocomplex. In certain embodiments, the enzyme is alkaline phosphatase, horseradish peroxidase, or acetylcholine esterase.

In certain embodiments of the invention, an elevated level of PAG-55 protein fraction above a selected cut-off or baseline, indicates or confirms that an animal is pregnant. The cut-off value is selected so as to provide a minimal number of false-positive and/or false-negative results while simultaneously providing early detection in accordance with the present invention. In certain embodiments, the level of PAG-55 protein fraction selected for determination that an animal is pregnant is any detectable level greater than about 0.0 ng/ml of serum. Generally, the baseline levels of PAG-55 protein fraction range from about 0.01 ng/ml to about 2 ng/ml. Thus, in one embodiment of the present invention the cut-off level is about 2 ng/ml, making elevated PAG-55 levels any level that is greater than about 2 ng/ml. In certain embodiments, the level of PAG-55 protein fraction is from about 1.0 ng/ml to about 5 ng/ml of serum. In other embodiments of the invention, the level of PAG-55 protein fraction is at least about 2.0 ng/ml to about 3.0 ng/ml of serum.

In another embodiment, measuring PAG-55 levels may comprise, for example, nucleic acid hybridization, including Northern blotting and wherein the nucleic acid hybridization comprises amplification. The amplification may comprise RT-PCR.

Certain embodiments of the invention also include measuring the level of progesterone in the sample, and wherein elevated levels of PAG-55 protein fraction and progesterone indicate that said animal is pregnant. This method may further comprise measuring the progesterone levels by immunologic detection. These methods may include conditions wherein the monoclonal antibody preparation comprises a first monoclonal anti-PAG-55 antibody and a second monoclonal anti-progesterone antibody.

Similarly, these methods may include conditions wherein the ELISA is a sandwich ELISA comprising forming an immunocomplex between PAG-55 protein fraction and progesterone proteins with a first antibody preparation fixed to a substrate and binding a second antibody preparation labeled with an enzyme to the immunocomplex. In certain embodiments, the enzyme is alkaline phosphatase, horseradish peroxidase, or acetylcholine esterase. In certain embodiments of the invention, the elevated level of progesterone that is detected is at least about 1 ng/ml of serum. In certain preferred aspects of this embodiment the elevated level of progesterone is at least about 2 ng/ml of serum.

In certain embodiments of the invention, the level of PAG-55 protein fraction and progesterone will be measured, and elevated levels of PAG-55 protein fraction and progesterone indicate that the animal is pregnant. In certain embodiments of these methods, the elevated level of progesterone is above about 2 ng/ml of serum. In other embodiments of the invention, the elevated level of progesterone is above about 3 ng/ml of serum. Additionally, in certain embodiments the methods include measuring progesterone levels comprising measuring progesterone biosynthesis pathway enzyme levels by nucleic acid hybridization, immunologic detection, or enzyme activity measurement.

In certain embodiments of the invention, a sample is obtained at about day 20 through about day 30 post-insemination or any later days in gestation, and the elevated levels of PAG-55 protein fraction are those greater than about 0.0 ng/ml of serum, and includes those greater than about 0.5 ng/ml of serum, or greater than about 1 ng/ml of serum, or greater than about 2 ng/ml of serum (in a certain embodiment the levels of PAG-55 protein fraction range from about 0.5 ng/ml to 30 ng/ml of serum), and wherein the elevated levels of progesterone include those of at least about 1 ng/ml of serum (preferably at least about 2 ng/ml of serum, including levels of about 3 ng/ml or above about 3 ng/ml serum) or greater levels. In a more particular aspect of this embodiment the sample is obtained between about day 18 and about day 23 after insemination. In an even more particular aspect of this embodiment the sample is obtained between about day 18 and about day 20.

In certain embodiments of the present invention, a positive control sample may also be obtained from a pregnant animal (such as a bovine), as may a negative control sample from a non-pregnant animal (such as a bovine). The method may further comprise measuring the PAG-55 protein fraction and progesterone levels from a second sample from the animal at a second point in time.

In another embodiment, the invention provides a method of making a breeding decision for an ungulate animal comprising: (a) obtaining a sample from said animal, wherein said animal is suspected of being pregnant; (b) measuring the level of PAG-55 protein fraction in the sample; and (c) measuring the level of progesterone in the sample, wherein: (i) elevated levels of PAG-55 protein fraction and progesterone indicate that said animal is pregnant; (ii) non-elevated levels of PAG-55 protein fraction and progesterone indicate that said animal is not pregnant, and the animal should receive follow up hormone therapy for re-breeding; or (iii) elevated levels of PAG-55 protein fraction and non-elevated levels of progesterone indicate that said animal is not pregnant due to a non-viable embryo and the animal should receive follow up hormone therapy for re-breeding; or (iv) non-elevated levels of PAG-55 protein fraction and elevated levels of progesterone indicate that said animal is not pregnant, and the animal should receive follow up hormone therapy for re-breeding.

These methods may further comprise in step (ii) injecting the animal with gonadotropin-releasing hormone (GnRH), and about seven days later, injecting with prostaglandin $F_{2\alpha}$ (PGF), followed by re-insemination. In certain embodiments, these methods may further comprise in step (iii) injecting the animal with GnRH, and about seven days later, injecting the animal with PGF, followed by re-insemination. In other embodiments these methods may further comprise in step (iv) injecting the animal with PGF, followed by re-insemination.

Further embodiments of the invention may include in steps (ii), (iii) or (iv), about 48 hours after PGF injection and before re-insemination, administering a second injection of GnRH. Additionally, the method may also further comprise, prior to step (a), inseminating the bovine animal. Further embodiments of the invention include methods wherein said PGF injection is administered at day 20 post-insemination and wherein said re-insemination is carried out at day 28 post-insemination. Optionally, embodiments of the invention include methods wherein said PGF injection is administered at day 26 post-insemination and wherein re-insemination is carried out at day 28 post-insemination.

Additional embodiments of the present invention include a method of making a breeding decision for an ungulate animal comprising (a) obtaining a sample from said animal, wherein said animal is suspected of being pregnant; and (b) measuring the level of PAG-55 protein fraction in said sample; wherein: (i) elevated levels of PAG-55 protein fraction levels indicate that said animal is pregnant; or (ii) non-elevated levels of PAG-55 protein fraction indicate that said animal is not pregnant and, the animal should receive appropriate hormone therapy for re-breeding. Such methods may further comprise in step (ii) injecting the animal with gonadotropin-releasing hormone (GnRH), and about seven days later, injecting with prostaglandin $F_{2\alpha}$ (PGF), followed by re-insemination. These methods may further comprise in step (ii) injecting the animal with PGF, followed by re-insemination.

Various embodiments contemplate methods for the diagnosis of pregnancy in ruminants and methods for making breeding decisions in ruminants involving the detection of the levels of PAG-55 protein fraction in a biological sample, either by itself, or in combination with a second antigen and the second antigen may be progesterone or some other pregnancy-specific antigen.

Embodiments of the present invention also include an isolated acidic PAG-55 protein fraction purified from about day 55 to about day 60 ungulate placentae. In particular embodiments, the isolated acidic PAG-55 protein fraction is isolated from bovine placentae. Embodiments of the invention also include purified antibodies generated by using the PAG-55 protein fraction, as an immunogen. Embodiments of the invention may further include a mixture of purified antibodies, in any combination, generated from any of the PAG-55 protein fraction components, such as PAG-4, PAG-6, PAG-9, PAG-16, PAG-18, PAG-19, and/or Mon PAG. Further aspects of the invention include an immunodetection kit comprising in suitable container means, the antibody of the present invention, and an immunodetection reagent. Aspects of the invention also include a purified antibody of the present invention operably attached to a detectable label.

Embodiments of the present invention also include methods of isolating acidic PAG-55 protein fraction from an ungulate animal comprising a) obtaining and homogenizing tissue from about day 50 to about day 60 ungulate placentae; b) isolating an acidic PAG protein fraction from said tissue by performing affinity chromatography and collecting acidic eluates therefrom; c) purifying the PAG-55 protein fraction in the acidic eluates by gel filtration chromatography and collecting the filtrates; and d) identifying the PAG-55 protein fraction obtained in step c, by immunodetection.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 5A and 5B show a polyacrylamide gel of the PAG 55 protein fraction; FIG. 5A showing the silver stained gel and FIG. 5B showing the Western blot using anti-PAG antibodies.

FIG. 6 shows a 2-Dimensional polyacrylamide gel analysis of day 55 PAG protein fraction antigens.

FIG. 7 shows the partial nucleotide sequence and predicted amino acid sequences of pMONPAG.

FIGS. 8A, 8B and 8C describes the peptide content of the spots from the 2-D gel analysis of the PAG 55 protein fraction.

DETAILED DESCRIPTION OF THE INVENTION

Figure 1A:
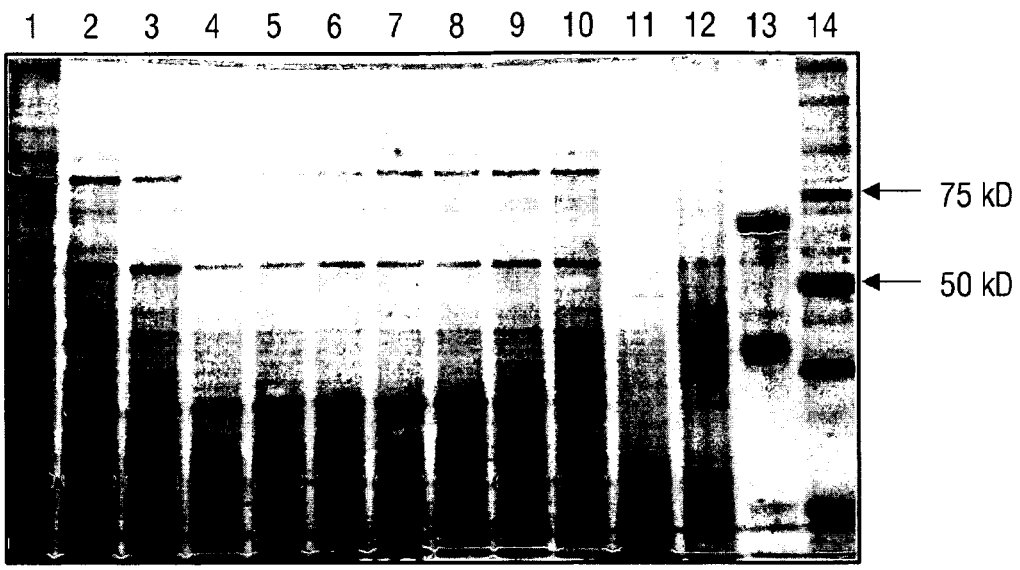
FIGS. 1A and 1B show SDS-PAGE and a Western blot of the day 55 PAG protein fraction.

The invention overcomes the limitations of the prior art by providing a reliable test for early pregnancy diagnosis and methods for use thereof. A reliable yet simple pregnancy test for ungulates, especially for ruminants such as cattle has long been sought. Typical prior tests have either not allowed early detection of pregnancy or have suffered from a high incidence of false positive or false negative results. The prior tests, although potentially useful, have thus fallen short of expectations in terms of their practical, on-farm use. As a result of these shortcomings the animals remain "open" for two or three estrous cycles. The present invention minimizes this "open" time by allowing for the determination of pregnancy, or non-pregnancy, as early as the first estrus following a breeding attempt.

Various embodiments of the present invention overcome the limitations of the prior art by detecting the presence and level of PAG-55 protein or proteins in a biological sample of an animal suspected of being pregnant. More particularly, the present invention involves an acidic protein fraction purified from about day 55 to day 60 of ungulate placenta, particularly from bovine placenta. This acidic PAG fraction, isolated from about day 55 to about day 60 is enriched for more "early PAG-proteins" or antigens when compared to fractions purified from about day 80 to about day 100 bovine placenta. Thus, this enriched fraction is referred to as "PAG-55", "PAG-55 protein/s", "PAG-55 antigen/s", or "PAG-55 protein fraction" and encompasses the proteins and antigens present in this acidic fraction. While these PAG-55 antigens are preferably isolated from about day 55 through about day 60 of bovine placenta, it is possible that the PAG-55 antigens may be present in earlier placental tissue. The range of from about day 55 through about day 60 of ungulate placenta is preferable for isolating the PAG-55 protein fraction since there is a desirable quantity of placental tissue present at this stage of pregnancy. The PAG-55 enriched fraction is utilized to generate polyclonal and monoclonal antibodies suitable for detecting pregnancy in cows bred from day 45 postpartum. The polyclonal and/or monoclonal antibodies that are generated using the acidic, PAG-55 enriched protein fraction as an immunogen will be useful for detecting pregnancy prior to day 30 (from about day 15 to the end of gestation) and will have the added benefit of being able to accurately detect pregnancy in cows bred from day 45 post-partum.

The present invention will also facilitate detection of PAG-55 proteins in serum. Various embodiments of the present invention comprise methods or means (including kits) for allowing the detection of the PAG-55 proteins or any antigenic component thereof, in whole blood samples that are allowed to clot. The extruded serum from the clotted blood then used in a desired immunodetection method for evaluating the presence and/or amount of the PAG-55 proteins in the sample in order to determine whether or not the animal is pregnant.

The PAG-55 protein fraction may be analyzed by itself to determine the pregnancy status of the animal suspected of being pregnant. In a particularly preferred aspect of this embodiment of the invention, the PAG-55 protein fraction levels are analyzed immunologically by detecting the PAG-55 protein fraction levels with at least one antibody, or several antibodies, either polyclonal or monoclonal, that were raised to PAG-55 protein fraction (either to fragments or to full-length PAG-55 protein/s or synthetic peptide antigens, either native or recombinant protein). In an even more preferred aspect of this embodiment the antibody specifically recognizes either specific epitopes of PAG-55 proteins or full length PAG-55 protein/s. In a preferred embodiment, the presence of detectable PAG-55 protein fraction above background levels in the maternal circulation indicates the presence of a conceptus in the uterus.

Alternatively, in other embodiments of the present invention, the PAG-55 protein fraction levels present in the biological samples may be determined in conjunction with the determination of the levels of one, or more other pregnancy specific compounds.

In one preferred embodiment, the level of PAG-55 protein fraction is determined in conjunction with a determination of the progesterone level in a biological sample from the same animal in order to provide for the early and accurate diagnosis of pregnancy in bovine and other ruminants. By assaying for both the progesterone and PAG-55 protein fraction, pregnancy diagnosis is possible with a high degree of accuracy. This is because the combined test measures a protein component produced by the conceptus and a maternal component, progesterone, both of which are elevated upon the establishment of a successful pregnancy in ruminant species such as cattle. This finding is significant because pregnancy diagnosis is an important component in reproductive management of livestock, particularly in the dairy industry where a high proportion of artificial inseminations fail and additional days open reduce the net operating income to the producer.

Various embodiments of the present invention comprise a method and means (including kits) for the diagnosis of pregnancy or non-pregnancy in an animal suspected of being in the early stages of pregnancy. In particular aspects of these embodiments the subject animal is a ruminant selected from the group consisting of bovine, ovine, and caprine. In an even more particular aspect of this embodiment the animal is bovine. In the most preferred aspect of this embodiment the animal is a dairy heifer, a dairy cow, or a beef cow.

In some embodiments of the present invention the diagnosis of pregnancy or non-pregnancy is made by analyzing a biological sample from the animal suspected of being in the early stages of pregnancy. The analysis is done by detecting the presence of the PAG-55 protein fraction and optionally, the amount of progesterone in the biological sample from animals, including bovines, suspected of being in the early stages of pregnancy. In various embodiments the biological sample comprises serum, plasma, blood, saliva, urine, milk, or any other suitable sample from the subject animal, as long as the sample is compatible with the present invention. In one particularly preferred embodiment the biological sample is from blood, serum, or plasma.

In various embodiments of the invention the biological sample is obtained from the animal suspected of being pregnant from 15 to 30 days after natural breeding or artificial insemination has occurred. Preferably, the sample may be collected at any of days 15, 16, 17, 18, 19, 20, 21, 22, 23, 24, 25, 26, 27, 28, 29, or day 30 after breeding or even later. More preferably the sample may be collected at about days 20 to 30 after breeding, and even more preferably 20-25 days after breeding.

In various embodiments of the present invention the animal whose pregnancy status is to be determined is a ruminant. More preferably the animal is a bovine, ovine, or caprine animal (where bovine includes cows, ovine includes sheep, and caprine includes goats). Even more preferably the animal is bovine and most preferably the animal is a beef or dairy cow.

In various embodiments of the invention, the pregnancy test is carried out by detecting PAG-55 protein fraction and, optionally, progesterone by immunological methods. For example, by using monoclonal or polyclonal antibodies raised against intact PAG-55 protein fraction (or alternatively antibodies against peptides comprising immunoreactive epitopes of PAG-55 protein/s). In a preferred aspect of this embodiment the antibodies (monoclonal or polyclonal) are raised against either full-length native or full-length recombinant PAG-55 protein/s. Most preferably the immunogen is full-length bovine PAG-55 protein/s and the antibodies are monoclonal antibodies.

For immunological progesterone analysis, commercially available assay kits are available that may be used to measure serum levels of progesterone. Using a PAG-55 protein fraction assay and the commercial progesterone assay, it was found that pregnancy detection could be performed as early as about day 23 in cattle or during peri-implantation in ruminants, generally. Additionally, the present invention is beneficial in that it results in a very low rate (<5%) of false positive and false negative results.

According to the present invention, determining that PAG-55 proteins in combination with progesterone are expressed in early stages of pregnancy is useful for detection of pregnancy at an early stage. In cattle, detection of PAG-55 proteins may be used individually or in combination with other diagnostic methods to provide a diagnostic evaluation of pregnancy. It is envisioned that PAG-55 enriched fractions from other species, will also prove useful, alone or in combination, for similar purposes.

The serum progesterone concentration in the pregnant cows is about 3 ng/ml or above on day 16 and continues to rise, thereafter. If a cow is not pregnant, the serum progesterone concentration declines significantly from day 16 onwards and drops to below 3 ng/ml (in most cases below 1.0 ng/ml) by day 19 to day 23 (Santos et al., 2002; Ayalon, 1978; Weibold, 1988).

Chandrasekaran et al., 1990 have shown that levels of progesterone in the milk correlate with serum progesterone levels, although they are three-fold lower, suggesting that analysis of milk progesterone levels is also applicable for use according to the instant invention.

One embodiment of the present invention is directed to a method comprising a combined testing for the PAG-55 protein fraction and progesterone used to determine the pregnancy status of a cow. According to one particular aspect of this embodiment, the presence of the PAG-55 protein fraction above a zero threshold level (e.g. >0.0 ng/ml) along with a serum progesterone value of from above 2 ng/ml, indicate that a cow is pregnant. In an especially preferred aspect of this embodiment the serum progesterone level is about 3 ng/ml or higher. In contrast, if PAG-55 protein fraction is absent in the serum or present at a level below the "threshold level" and the animal has a serum progesterone value below about 2-5 ng/ml, and preferably below about 3 ng/ml, the animal is considered to be not pregnant or "open." Table 1 shows how the sample levels will be used to diagnose or predict the pregnancy status.

The specificity of pregnancy diagnosis with the combination testing would likely improve when testing is done from day 16 to the end of gestation, since serum progesterone values of ~80% of open dairy cows are below 2 ng/ml from days 20 to 23.

TABLE 1

| Sample levels | Predicted Pregnancy Status |
| --- | --- |
| PAG-55 protein fraction positive (+, above baseline) Progesterone 3 ng/ml or above | Pregnancy positive |
| PAG-55 protein fraction negative Progesterone below 3 ng/ml | Pregnancy negative |

The specificity and sensitivity of the combined test is likely to range from 75 to 100% when testing is done from about day 23 to the end of gestation.

Particular aspects of this embodiment include determination of the PAG-55 protein fraction or detection of any of the antigenic components of the PAG-55 protein fraction and, optionally, progesterone levels using immunological and/or nucleic acid based methods. These various detection methods are well known and widely used in the art.

A. Immunologic Detection of PAG-55 Protein Fraction and/or Progesterone.

Contemplated embodiments of the present invention include those employing the use of antibodies in the immunologic detection of the PAG-55 protein fraction or detection of any of the antigenic components of the PAG-55 protein fraction and, optionally, progesterone. Various useful immunodetection methods have been described in the scientific literature, such as, e.g., Nakamura et al. (1987; incorporated herein by reference). Immunoassays, in their most simple and direct sense, are binding assays. Certain preferred embodiments may include the use of immunoassays including various types of enzyme linked immunosorbent assays (ELISAs), radioimmunoassays (RIA), biosensors, or the use of lateral flow technology based diagnostic systems. Immunohistochemical detection using tissue sections also is contemplated as useful for the present invention. However, it will be readily appreciated that detection is not limited to such techniques, and Western blotting, dot blotting, FACS analyses, and the like also may be used in connection with the present invention.

In general, immunobinding methods include obtaining a sample suspected of containing a protein, peptide or antibody, and contacting the sample with an antibody or protein or peptide in accordance with the present invention, as the case may be, under conditions effective to allow the formation of immunocomplexes. Preferred samples, according to the present invention, are fluids, such as milk, urine, blood, serum, plasma, or saliva.

Contacting the selected biological sample with the protein, peptide or antibody under conditions effective and for a period of time sufficient to allow the formation of immune complexes (primary immune complexes) is generally a matter of simply adding the composition to the sample and incubating the mixture for a period of time long enough for the antibodies to form immune complexes with PAG-55 protein fraction or progesterone. After this time, the PAG-55 protein fraction or progesterone antibody mixture will be washed to remove any non-specifically bound antibody species, allowing only those antibodies specifically bound within the primary immune complexes to be detected.

In general, the detection of immunocomplex formation is well known in the art and may be achieved through the application of numerous approaches. These methods are generally based upon the detection of a label or marker, such as any radioactive, fluorescent, biological or enzymatic tags or labels of standard use in the art. U.S. patents concerning the use of such labels include U.S. Pat. Nos. 3,817,837; 3,850,752; 3,939,350; 3,996,345; 4,277,437; 4,275,149 and 4,366,241, each incorporated herein by reference. Of course, one may find additional advantages through the use of a secondary binding ligand such as a second antibody or a biotin/avidin ligand binding arrangement, as is known in the art.

Usually, the primary immune complexes may be detected by means of a second binding ligand that has binding affinity for the PAG-55 or progesterone-specific first antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under conditions effective and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two step approach. A second binding ligand, such as an antibody, that has binding affinity for the PAG-55 or progesterone antibody is used to form secondary immune complexes, as described above. The second binding ligand contains an enzyme capable of processing a substrate to a detectable product and, hence, amplifying signal over time. After washing, the secondary immune complexes are contacted with substrate, permitting detection.

Progesterone can also be detected in accordance with the invention using various commercially available detection kits. For example, the COAT-A-COUNT™ progesterone kit used by the inventors, which is available from Diagnostics Products Corporation (Los Angeles, Calif.). Examples of other assays that have been described include the immunoenzymatic technique described, for example, by Stefanakis et al., (1994) and by Stanley et al. (1986); and salivary progesterone level assays described, for example, by Lu et al., (1997) and Vienravi et al., 1994.

B. ELISA

In one particularly preferred embodiment of the present invention, the PAG-55 protein fraction or any of the antigenic components of the PAG-55 protein fraction detected is bovine PAG-55 protein fraction which along with progesterone are detected using monoclonal or polyclonal antibodies to either the PAG-55 protein fraction or progesterone as part of an ELISA.

Thus as a part of the practice of the present invention, the widely known and well-understood principles of an enzyme-linked immunoassay (ELISA) may be used. ELISA was first introduced by Engvall and Perlmann (1971) and has become a powerful analytical tool using a variety of protocols (Engvall, 1980; Engvall, 1976; Engvall, 1977; Gripenberg et al., 1978; Sarngadharan et al., 1984). ELISA allows for substances to be passively adsorbed to solid supports such as plastic to enable facile handling under laboratory conditions. For a comprehensive treatise on ELISA the skilled artisan is referred to "ELISA; Theory and Practice" (Crowther, 1995 incorporated herein by reference).

The sensitivity of ELISA methods is dependent on the turnover of the enzyme used and the ease of detection of the product of the enzyme reaction. Enhancement of the sensitivity of these assay systems can be achieved by the use of fluorescent and radioactive substrates for the enzymes. Immunoassays encompassed by the present invention include, but are not limited to those described in U.S. Pat. No. 4,367,110 (double monoclonal antibody sandwich assay) and U.S. Pat. No. 4,452,901 (western blot). Other assays include immunoprecipitation of labeled ligands and immunocytochemistry, both in vitro and in vivo.

In a particularly preferred embodiment, the invention comprises a "sandwich" ELISA, where anti-PAG-55 antibodies, are immobilized onto a selected surface, such as a well in a polystyrene microtiter plate or a dipstick. Then, a test composition suspected of containing PAG-55 protein fraction, e.g., a clinical sample, such as blood or serum, is contacted with the surface. After binding and washing to remove non-specifically bound immunocomplexes, the bound antigen may be detected by a second antibody to the PAG-55.

In another exemplary ELISA, polypeptides from the sample are immobilized onto a surface and then contacted with the anti-PAG-55 antibodies. After binding and washing to remove non-specifically bound immune complexes, the bound antibody is detected. Where the initial antibodies are linked to a detectable label, the primary immune complexes may be detected directly. Alternatively, the immune complexes may be detected using a second antibody that has binding affinity for the first antibody, with the second antibody being linked to a detectable label.

Another ELISA in which the PAG-55 is immobilized involves the use of antibody competition in the detection. In this ELISA, labeled antibodies are added to the wells, allowed to bind to the PAG-55, and detected by means of their label. The amount of PAG-55 protein fraction in a sample is determined by mixing the sample with the labeled antibodies before or during incubation with coated wells. The presence of PAG-55 protein fraction in the sample acts to reduce the amount of antibody available for binding to the well, and thus reduces the ultimate signal.

Irrespective of the format employed, ELISAs have certain features in common, such as coating, incubating or binding, washing to remove non-specifically bound species, and detecting the bound immune complexes. In coating a plate with either antigen or antibody, one will generally incubate the wells of the plate with a solution of the antigen or antibody, either overnight or for a specified period of hours. The wells of the plate will then be washed to remove incompletely adsorbed material. Any remaining available surfaces of the wells are then "coated" with a nonspecific protein that is antigenically neutral with regard to the test antisera. These include normal rabbit serum, bovine serum albumin (BSA), casein and solutions of milk powder. The coating allows for blocking of nonspecific adsorption sites on the immobilizing surface and thus reduces the background caused by nonspecific binding of antisera onto the surface.

In ELISAs, it is probably more customary to use a secondary or tertiary detection means rather than a direct procedure. Thus, after binding of a protein or antibody to the well, coating with a non-reactive material to reduce background, and washing to remove unbound material, the immobilizing surface is contacted with the control human cancer and/or clinical or biological sample to be tested under conditions effective to allow immune complex (antigen/antibody) formation. Detection of the immune complex then requires a labeled secondary binding ligand or antibody, or a secondary binding ligand or antibody in conjunction with a labeled tertiary antibody or third binding ligand.

"Under conditions effective to allow immune complex (antigen/antibody) formation" means that the conditions preferably include diluting the antigens and antibodies with solutions such as normal rabbit serum, BSA, bovine gamma globulin (BGG), evaporated or powdered milk, and phosphate buffered saline (PBS)/TWEEN™. These added agents also tend to assist in the reduction of nonspecific background.

The "suitable" conditions also mean that the incubation is at a temperature and for a period of time sufficient to allow effective binding. Incubation steps are typically from times ranging from about 1 hour (h), to 2 hours and even up to about 4 hrs., at temperatures preferably on the order of about 25° C. to about 27° C., or even overnight at approximately 4° C.

To provide a detecting means, the second or third antibody will have an associated label to allow detection. Preferably, this will be an enzyme that will generate color development upon incubating with an appropriate chromogenic substrate.

Thus, for example, one will desire to contact and incubate the first or second immune complex with a urease, glucose oxidase, alkaline phosphatase or hydrogen peroxidase-conjugated antibody for a period of time and under conditions that favor the development of further immunecomplex or immunocomplex formation (e.g., incubation for 2 h at room temperature in a PBS-containing solution such as PBS-Tween).

After incubation with the labeled antibody, and subsequent to washing to remove unbound material, the amount of label is quantified, e.g., by incubation with a chromogenic substrate such as urea and bromocresol purple or 2,2'-azido-di-(3-ethyl-benzthiazoline-6-sulfonic acid [ABTS] and $H_2O_2$, in the case of peroxidase as the enzyme label. Quantitation is then achieved by measuring the degree of color generation, e.g., using a visible spectrophotometer.

A variant of ELISA is the enzyme-linked coagulation assay, or ELCA (U.S. Pat. No. 4,668,621), which uses the coagulation cascade combined with the labeling enzyme RVV-XA (Russell's viper venum factor X activator) as a universal detection system. The advantage of this system for the current invention, is that the coagulation reactions can be performed at physiological pH in the presence of a wide variety of buffers. It is therefore possible to retain the integrity of complex analytes.

C. Nucleic Acid Detection

In some embodiments of the instant invention, it will be desirable to detect nucleic acids (mRNAs or cDNAs) which encode any antigenic components of the PAG-55 protein fraction, and/or which encode proteins involved in the biosynthesis of progesterone to determine the levels of the corresponding proteins. Such methods include RNase protection assays, Northern blot assays and RT-PCR. The following describe methods relevant to the detection and quantification of such nucleic acids.

1. Hybridization

The use of a probe or primer of between 13 and 100 nucleotides, preferably between 17 and 100 nucleotides in length, or in some aspects of the invention up to 1-2 kilobases or more in length, allows the formation of a duplex molecule that is both stable and selective. Molecules having complementary sequences over contiguous stretches greater than 20 bases in length are generally preferred, to increase stability and/or selectivity of the hybrid molecules obtained. One will generally prefer to design nucleic acid molecules for hybridization having one or more complementary sequences of 20 to 30 nucleotides, or even longer where desired. Such fragments may be readily prepared, for example, by directly synthesizing the fragment by chemical means or by introducing selected sequences into recombinant vectors for recombinant production.

Accordingly, the nucleotide sequences of the invention may be used for their ability to selectively form duplex molecules with complementary stretches of DNAs and/or RNAs or to provide primers for amplification of DNA or RNA from samples. Depending on the application envisioned, one would desire to employ varying conditions of hybridization to achieve varying degrees of selectivity of the probe or primers for the target sequence.

For applications requiring high selectivity, one will typically desire to employ relatively high stringency conditions to form the hybrids. For example, relatively low salt and/or high temperature conditions, such as provided by about 0.02 M to about 0.10 M NaCl at temperatures of about 50° C. to about 70° C. Such high stringency conditions tolerate little, if any, mismatch between the probe or primers and the template or target strand and would be particularly suitable for isolating specific genes or for detecting specific mRNA transcripts. It is generally appreciated that conditions can be rendered more stringent by the addition of increasing amounts of formamide.

Conditions may be rendered less stringent by increasing salt concentration and/or decreasing temperature. For example, a medium stringency condition could be provided by about 0.1 to 0.25 M NaCl at temperatures of about 37° C. to about 55° C., while a low stringency condition could be provided by about 0.15 M to about 0.9 M salt, at temperatures ranging from about 20° C. to about 55° C. Hybridization conditions can be readily manipulated depending on the desired results.

In other embodiments, hybridization may be achieved under conditions of, for example, 50 mM Tris-HCl (pH 8.3), 75 mM KCl, 3 mM $MgCl_2$, 1.0 mM dithiothreitol, at temperatures between approximately 20° C. to about 37° C. Other hybridization conditions utilized could include approximately 10 mM Tris-HCl (pH 8.3), 50 mM KCl, 1.5 mM $MgCl_2$, at temperatures ranging from approximately 40° C. to about 72° C.

In certain embodiments, it will be advantageous to employ nucleic acids of defined sequences of the present invention in combination with an appropriate means, such as a label, for determining hybridization. A wide variety of appropriate indicator means are known in the art, including fluorescent, radioactive, enzymatic or other ligands, such as avidin/biotin, which are capable of being detected. In preferred embodiments, one may desire to employ a fluorescent label or an enzyme tag such as urease, alkaline phosphatase or peroxidase, instead of radioactive or other environmentally undesirable reagents. In the case of enzyme tags, colorimetric indicator substrates are known that can be employed to provide a detection means that is visibly or spectrophotometrically detectable, to identify specific hybridization with complementary nucleic acid containing samples.

In general, it is envisioned that the probes or primers described herein will be useful as reagents in solution hybridization, as in PCR™, for detection of expression of corresponding genes, as well as in embodiments employing a solid phase. In embodiments involving a solid phase, the test DNA (or RNA) is adsorbed or otherwise affixed to a selected matrix or surface. This fixed, single-stranded nucleic acid is then subjected to hybridization with selected probes under desired conditions. The conditions selected will depend on the particular circumstances (depending, for example, on the G+C content, type of target nucleic acid, source of nucleic acid, size of hybridization probe, etc.). Optimization of hybridization conditions for the particular application of interest is well known to those of skill in the art. After washing of the hybridized molecules to remove non-specifically bound probe molecules, hybridization is detected, and/or quantified, by determining the amount of bound label. Representative solid phase hybridization methods are disclosed in U.S. Pat. Nos. 5,843, 663, 5,900,481 and 5,919,626. Other methods of hybridization that may be used in the practice of the present invention are disclosed in U.S. Pat. Nos. 5,849,481, 5,849,486 and 5,851,772. The relevant portions of these and other references identified in this section of the Specification are incorporated herein by reference.

2. Amplification of Nucleic Acids.

Nucleic acids used as a template for amplification may be isolated from cells, tissues or other samples according to standard methodologies found in Sambrook et al., 1989, Sambrook et al., 2001, and Ausubel et al. 2002, the teachings of which are incorporated herein by reference. In certain embodiments, analysis is performed on whole cell or tissue homogenates or biological fluid samples without substantial purification of the template nucleic acid. The nucleic acid may be genomic DNA or fractionated or whole cell RNA. Where RNA is used, it may be desired to first convert the RNA to a complementary DNA.

The term "primer," as used herein, is meant to encompass any nucleic acid that is capable of priming the synthesis of a nascent nucleic acid in a template-dependent process. Typically, primers are oligonucleotides from ten to twenty and/or thirty base pairs in length, but longer sequences can be employed. Primers may be provided in double-stranded and/or single-stranded form, although the single-stranded form is preferred.

Pairs of primers designed to selectively hybridize to nucleic acids corresponding to a segment, portion, or entire region that encodes any of the immunogenic PAG-55 proteins useful for detecting pregnancy may be contacted with a sample/test template nucleic acid under conditions that permit selective hybridization. Depending upon the desired application, high stringency hybridization conditions may be selected that will only allow hybridization to sequences that are completely complementary to the primers. In other embodiments, hybridization may occur under reduced stringency to allow for amplification of nucleic acids contain one or more mismatches with the primer sequences. Once hybridized, the template-primer complex is contacted with one or more enzymes that facilitate template-dependent nucleic acid synthesis. Multiple rounds of amplification, also referred to as "cycles," are conducted until a sufficient amount of amplification product is produced.

The amplification product may be detected or quantified. In certain applications, the detection may be performed by visual means. Alternatively, the detection may involve indirect identification of the product via chemiluminescence, radioactive scintigraphy of incorporated radiolabel or fluorescent label or even via a system using electrical and/or thermal impulse signals (Affymax technology; Bellus, 1994).

A number of template dependent processes are available to amplify the oligonucleotide sequences present in a given template sample. One of the best known amplification methods is the polymerase chain reaction (referred to as PCR™) which is described in detail in U.S. Pat. Nos. 4,683,195, 4,683,202 and 4,800,159, and in Innis et al., 1988, each of which is incorporated herein by reference in their entirety.

A reverse-transcriptase coupled PCR™ amplification procedure may be performed to quantify the amount of mRNA amplified. Methods of reverse transcribing RNA into cDNA are well known (see Sambrook et al., 1989). Alternative methods for reverse transcription utilize thermostable DNA polymerases. These methods are described in WO 90/07641. Polymerase chain reaction methodologies are well known in the art. Representative methods of RT-PCR are described in U.S. Pat. No. 5,882,864.

Another method for amplification is ligase chain reaction ("LCR"), disclosed in European Application No. 320 308, incorporated herein by reference in its entirety. U.S. Pat. No. 4,883,750 describes a method similar to LCR for binding probe pairs to a target sequence. A method based on PCR™ and oligonucleotide ligase assay (OLA), disclosed in U.S. Pat. No. 5,912,148, may also be used.

Alternative methods for amplification of target nucleic acid sequences that may be used in the practice of the present invention are disclosed in U.S. Pat. Nos. 5,843,650, 5,846,709, 5,846,783, 5,849,546, 5,849,497, 5,849,547, 5,858,652, 5,866,366, 5,916,776, 5,922,574, 5,928,905, 5,928,906, 5,932,451, 5,935,825, 5,939,291 and 5,942,391, GB Application No. 2 202 328, and in PCT Application No. PCT/US89/01025, each of which is incorporated herein by reference in its entirety.

Qbeta Replicase, described in PCT Application No. PCT/US87/00880, may also be used as an amplification method in the present invention. In this method, a replicative sequence of RNA that has a region complementary to that of a target is added to a sample in the presence of an RNA polymerase. The polymerase will copy the replicative sequence which may then be detected.

An isothermal amplification method, in which restriction endonucleases and ligases are used to achieve the amplification of target molecules that contain nucleotide 5'-[alpha-thio]-triphosphates in one strand of a restriction site may also be useful in the amplification of nucleic acids in the present invention (Walker et al., 1992). Strand Displacement Amplification (SDA), disclosed in U.S. Pat. No. 5,916,779, is another method of carrying out isothermal amplification of nucleic acids which involves multiple rounds of strand displacement and synthesis, i.e., nick translation.

Other nucleic acid amplification procedures include transcription-based amplification systems (TAS), including nucleic acid sequence based amplification (NASBA) and 3SR (Kwoh et al., 1989; Gingeras et al., PCT Application WO 88/10315, incorporated herein by reference in their entirety). European Application No. 329 822 disclose a nucleic acid amplification process involving cyclically synthesizing single-stranded RNA ("ssRNA"), ssDNA, and double-stranded DNA (dsDNA), which may be used in accordance with the present invention.

PCT Application WO 89/06700 (incorporated herein by reference in its entirety) disclose a nucleic acid sequence amplification scheme based on the hybridization of a promoter region/primer sequence to a target single-stranded DNA ("ssDNA") followed by transcription of many RNA copies of the sequence. This scheme is not cyclic, i.e., new templates are not produced from the resultant RNA transcripts. Other amplification methods include "race" and "one-sided PCR" (Frohman, 1990; Ohara et al., 1989).

3. Detection of Nucleic Acids.

Following any amplification, it may be desirable to separate the amplification product from the template and/or the excess primer. In one embodiment, amplification products are separated by agarose, agarose-acrylamide or polyacrylamide gel electrophoresis using standard methods (Sambrook et al., 1989). Separated amplification products may be cut out and eluted from the gel for further manipulation. Using low melting point agarose gels, the separated band may be removed by heating the gel, followed by extraction of the nucleic acid.

Separation of nucleic acids may also be effected by chromatographic techniques known in art. There are many kinds of chromatography which may be used in the practice of the present invention, including adsorption, partition, ion-exchange, hydroxylapatite, molecular sieve, reverse-phase, column, paper, thin-layer, and gas chromatography as well as HPLC.

In certain embodiments, the amplification products are visualized. A typical visualization method involves staining of a gel with ethidium bromide and visualization of bands under UV light. Alternatively, if the amplification products are integrally labeled with radio- or fluorometrically-labeled nucleotides, the separated amplification products can be exposed to X-ray film or visualized under the appropriate excitatory spectra.

In one embodiment, following separation of amplification products, a labeled nucleic acid probe is brought into contact with the amplified marker sequence. The probe preferably is conjugated to a chromophore but may be radiolabeled. In another embodiment, the probe is conjugated to a binding partner, such as an antibody or biotin, or another binding partner carrying a detectable moiety.

In particular embodiments, detection is by Southern blotting and hybridization with a labeled probe. The techniques involved in Southern blotting are well known to those of skill in the art (see Sambrook et al., 1989). One example of the foregoing is described in U.S. Pat. No. 5,279,721, incorporated by reference herein, which discloses an apparatus and method for the automated electrophoresis and transfer of nucleic acids. The apparatus permits electrophoresis and blotting without external manipulation of the gel and is ideally suited to carrying out methods according to the present invention.

Other methods of nucleic acid detection that may be used in the practice of the instant invention are disclosed in U.S. Pat. Nos. 5,840,873, 5,843,640, 5,843,651, 5,846,708, 5,846,717, 5,846,726, 5,846,729, 5,849,487, 5,853,990, 5,853,992, 5,853,993, 5,856,092, 5,861,244, 5,863,732, 5,863,753, 5,866,331, 5,905,024, 5,910,407, 5,912,124, 5,912,145, 5,919,630, 5,925,517, 5,928,862, 5,928,869, 5,929,227, 5,932,413 and 5,935,791, each of which is incorporated herein by reference.

4. Kits

All the essential materials and/or reagents required for detecting PAG-55 protein fraction or detection of any of the antigenic components of the PAG-55 protein fraction and, optionally, progesterone in a sample may be assembled together in a kit. This generally will comprise a probe or primers designed to hybridize specifically to individual nucleic acids and/or antibodies capable of specifically recognizing the molecules of interest in the practice of the present invention. Also included may be enzymes suitable for detecting the interaction of the antibodies with the target antigens and/or enzymes for amplifying nucleic acids, including various polymerases (reverse transcriptase, Taq, etc.), deoxynucleotides and buffers to provide the necessary reaction mixture for amplification. Such kits may also include enzymes and other reagents suitable for detection of specific proteins/compounds or nucleic acids or amplification products and/or for detecting antibody/ligand interaction. Such kits generally will comprise, in suitable means, distinct containers for each individual reagent or enzyme as well as for each probe, primer pair, and/or antibody.

All the essential materials and/or reagents required for detecting any of the desired analytes, including any analyte that would be indicative of pregnancy, especially in ungulates, for example a PAG protein fraction or any of the antigenic components of the PAG-55 protein fraction and, optionally, progesterone in a whole blood sample may be assembled together in a kit. This generally will comprise a serum collector tube or other means for collecting and containing the blood sample and allowing the clotting to occur. Typical serum collector tubes include the Becton Dicksinson (BD, Franklin Lakes, N.J.) BD Vacutainer® Plus Plastic Serum Tubes that are coated with silicone and micronized silica particles to accelerate clotting. A silicone coating reduces adherence of red cells to tube walls. Another serum collector tube is a "gel tube" such as the BD Vacutainer® SST™ Serum Separation Tube.

In addition to the silica particles that act as a clot activator, the SST™ Serum Separation Tube contains a gel that forms a physical barrier between serum or plasma and blood cells After collection of the blood sample, BD Vacutainer® SST™ Serum Separation Tubes should be inverted about five times, and then allowed to separate for at least about 10, and preferably about 30 minutes, allowing for clotting of the whole blood sample. In the present invention, it has been determined that no centrifugation step is necessary. After the tube has been inverted, the time allowed for clotting is anytime between at least about 10 minutes and 30 minutes. Importantly, good, easily readable results according to the present invention are observed in the absence of centrifugation of the sample, with surprisingly clean results. Finally, the BD Vacutainer® SST™ Serum Separation Transport Tube contains double the amount of gel used in the regular SST™ tubes. This provides a thicker barrier between the serum and plasma that remains intact during transportation, thereby maintaining the quality of the sample for the lab analysis. This tube can also be used in a manner similar to that described for the regular SST™ tubes.

Another type of tube that could be useful in the present invention includes the BD Vacutainer™ Hemogard™ Thrombin glass evacuated blood collection tube (BD Thrombin) that contains thrombin as a clot activator. This tube can also be used without the centrifugation of samples, an important benefit in the farm setting.

Another type of tube that could be useful in the present invention includes the BD Vacutainer™ with EDTA as anticoagulant (purple cap) tube to obtain unclotted blood or plasma for detecting PAG-55 proteins.

III. Livestock Breeding Programs.

One advance of the current invention is that it allows early detection of pregnancy with a low incidence of false positive results. Early detection of pregnancy is important because it allows re-breeding of animals found to not be pregnant, thereby minimizing the period during which the animal is "open." A low incidence of false positives is necessary to allow implementation of an effective re-breeding protocol. Prior pregnancy tests typically either were unable effectively detect early pregnancy or exhibited high incidence of false positives.

A type of early pregnancy test which has been used is the detection of pregnancy associated antigens (PAGs). An advantage of this test is that it can be done from day 23 to the end of gestation. Prior to the present invention, the PAG proteins utilized for pregnancy detection remained detectable at least through day 65 in the post partum cow, leading to false positives and additional days open. FIG. 3 shows the levels of PAG protein detected by the UMC-M4 antibody (from the University of Missouri) as being about 10 ng/ml through day 65 postpartum. In contrast, the level of PAG-55 protein fraction detected by the anti-PAG-55 antibodies of the present invention, dropped from about 7 ng/ml at day 3 post-partum to 2 ng/ml at day 45 post-partum. Thus, the present PAG-55 protein fraction and anti PAG-55 antibodies represent an improved method for the detection of early pregnancy in cows that are bred within the post-partum period.

Additionally, the inventors have found that by analyzing progesterone levels in addition to PAG-55 protein fraction levels, a very low incidence (<5%) of false positives can be obtained. This combination testing provides a method for accurate pregnancy detection in situations where the embryo has died or is non viable, and there may still be some low level of detectable PAG-55 protein fraction in the samples. Since the corpus luteum regresses shortly after embryo death, a low level of progesterone along with a higher level of PAG-55 protein fraction would indicate that the cow is carrying a non-viable embryo. Thus, a cow with a dying embryo may have detectable PAG-55 protein fraction at day 25, but a low progesterone level. Because progesterone is an absolute requirement for establishing pregnancy, a cow with low serum progesterone cannot maintain pregnancy.

Another class of embodiments of the present invention provides for methods of making breeding decisions for ungulate animals. Preferably, the subject animals are ruminants, including bovine, ovine, and caprine. More preferably, the animals are beef or dairy cattle.

Methods of the present invention comprise obtaining a biological sample from an ungulate animal suspected of being pregnant. Preferably, the biological sample comprises a blood, serum, plasma, milk, urine, or saliva sample, but any other biological samples suitable for use with the present invention are also contemplated. In the case of cattle the sample is preferably collected about 15-30 days after natural breeding or artificial insemination (collectively, "breeding") has taken place. More preferably the sample is serum collected at about 25-30 days after breeding and most preferably the sample is collected at days 23 to the end of gestation. Next, the sample is analyzed to determine the levels of PAG-55 protein fractions and, optionally, progesterone present in the sample. If the level of PAG-55 protein fraction or any of the antigenic components of the PAG-55 protein fraction is elevated as compared to non-pregnant controls, the animal is determined to be pregnant and no further action need be taken. Similarly, if the level of PAG-55 protein fraction or any of the antigenic components of the PAG-55 protein fraction and progesterone are found to be elevated as compared with non-pregnant controls, the animal is determined to be pregnant and no further action need be taken.

Benefits of the current invention include that it allows easy and accurate early detection of pregnancy, does not require equipment such as centrifuges or the addition of chemical agents and can be carried out quickly and easily in the farm setting. The present methods utilizing clotted blood, allow for more accurate tests that can be easily conducted in the farm setting without special equipment.

Other embodiments of the present invention provide methods of making breeding decisions for ungulate animals. Preferably, the subject animals are ruminants, including bovine, ovine, and caprine. More preferably, the animals are beef or dairy cattle. These methods comprise obtaining a biological sample from an ungulate animal suspected of being pregnant. Preferably, the biological sample comprises whole blood, collected in a sample tube, and the uncentrifuged sample has been allowed to clot in the presence of one or more clotting agents such as thrombin, phospholipids, kaolin (e.g. clay material), micronized silica (e.g. polysiloxane), and calcium. By allowing the whole blood sample to clot, the serum will be extruded or separated from certain lytic components of the blood, including red blood cells. These lytic and red blood cell components normally interfere with the results of immunodetection assays, as they are absorbed onto the test membrane and cause smearing along the region where the test results appear. By allowing the blood sample to clot, the serum will rise to the top of the sample, and the desired immunodetection strip or membrane can then be placed in fluid communication or contact with this serum portion of the sample (the yellowish, clear top portion of the sample). The serum is substantially free from interfering lytic or red blood cell components, and the serum is absorbed into and flows along the test strip or membrane producing an easy to read result. The present methods involving allowing the blood to clot with a clotting agent in a sample tube, are easier and more practical for the farm-setting, since no additional equipment or chemicals are needed. Alternatively, the test strip could be placed in an unclotted blood sample, where the strip filters the cells and permits the flow of plasma along the test strip or membrane producing an easy to read result. Previous alternative methods involved centrifugation, stirring, heating, and other physical separation steps that required expensive equipment or additional chemicals. The present methods only require a tube that can function as a serum separator tube (e.g. SST tubes, or Hemogard Thrombin glass evacuated blood collection tubes (BD)) and an immunodetection means such as a lateral flow strip.

In the case of cattle, the whole blood sample may be collected at any time during gestation, and is typically collected about 15-30 days after natural breeding or artificial insemination (collectively, "breeding") has taken place. More preferably the sample is serum collected at about 25-30 days after breeding and most preferably the sample is collected at days 23 to the end of gestation. Next, after allowing the whole blood sample to clot, the sample is analyzed by any suitable immunodetection means to determine the levels of PAG protein fraction or to determine the levels of any of the antigenic components of the PAG-55 protein fraction and, optionally, progesterone present in the sample. If the level of PAG protein fraction or any of the antigenic components of the PAG-55 protein fraction is elevated as compared to non-pregnant controls, the animal is determined to be pregnant and no further action need be taken. Similarly, if the level of PAG protein fraction or any of the antigenic components of the PAG-55 protein fraction and progesterone are found to be elevated as compared with non-pregnant controls, the animal is determined to be pregnant and no further action need be taken.]

If the levels of neither PAG-55 protein fraction nor progesterone are elevated, this indicates that the animal is not pregnant and additional actions are required. First, the animal could be injected with gonadotropin-releasing hormone (GnRH), and about seven days later, injected with prostaglandin $F_{2\alpha}$ (PGF), followed by re-insemination.

If the level of PAG-55 protein fraction or any of the antigenic components of the PAG-55 protein fraction is elevated but the levels of progesterone are not elevated, this indicates that the animal is not pregnant, due to early embryonic loss or a failure in maternal recognition of pregnancy. In this instance the animal should be injected with GnRH, then about seven days later, injected with PGF, followed by re-insemination.

If the level of PAG-55 protein fraction is not elevated, but the level of progesterone is elevated, this indicates that the animal is not pregnant. The animal should be injected with PGF, followed by re-insemination.

In preferred aspects of this embodiment of the invention, those where either one alone or both the PAG-55 protein fraction (or antigenic components thereof) and progesterone levels are not elevated, the method further comprises administering a (second) dose of GnRH about 48 hours after the PGF injection and before re-insemination.

In one particularly preferred embodiment of the present invention an injection of GnRH at day 26 is followed by a PGF injection administered at day 33 post-insemination, and an injection of GnRH and re-insemination is carried out at day 35 post-insemination.

A. Estrus and Ovulation.

Dairy cows come into estrus about once every 21 days. Cows display characteristic behaviors during estrus. Dairy workers can identify cows in estrus by these characteristic behaviors. Cows ovulate an egg about 28 hours after the onset of estrus. Most dairy cows are inseminated artificially about 12 hours after the onset of estrus so that sperm are in the reproductive tract when the cow ovulates.

B. Efficiency of Reproduction in Dairy Cows.

Lactating dairy cows are monitored for estrus. They are inseminated when they come into estrus so that they can become pregnant and have another calf. The efficiency with which cows are detected in estrus is low. Only about 50% of cows in estrus are actually detected by producers. Of the cows detected in estrus and inseminated, only about 30% will become pregnant. Thus, only about 15% (50%×30%) of ovulations result in a pregnancy. Thus, dairy reproduction can be inefficient because cows in estrus are not always seen and those inseminated do not always get pregnant. Although most cows could theoretically be artificially inseminated once every 21 days, the true insemination interval on farms is typically once every 40 to 60 days. This lost time results in negative impact on dairy income because the extended "open" period reduces the economic efficiency as a result of the extended period between calves and the reduced milk production during the phase just prior to drying (dairy cattle reach peak lactation 85 to 115 days post partum). Thus, it is more profitable if the cattle become pregnant as soon as possible. Furthermore, the efficiency of reproduction has worsened since 1951 (Butler, 1998) because of consolidation of the dairy industry due to increased genetic potential for milk production. Larger farms and labor shortages have resulted in a reduction in the amount of time that the animals are observed and a consequential reduction in the detection of estrus. This is a significant problem as dairy reproduction is the key to the dairy farm's success. In fact the most common reason for culling of cows is that they do not become pregnant and are considered barren.

C. Corpus Luteum and Progesterone.

After a cow ovulates a corpus luteum (CL) is formed on the ovary and the CL secretes the hormone progesterone. Progesterone can be detected in the blood of the dam and is needed to maintain the pregnancy. If the egg is fertilized and the embryo grows and survives then the corpus luteum will be maintained until the end of gestation (about 280 days). If the egg is not fertilized or the embryo dies, then the corpus luteum will regress and the cow will reenter estrus cycle.

D. PAG-55 Protein Fraction and Pregnancy Testing.

Following conception the conceptus produces the antigens in the PAG-55 protein fraction. PAG-55 proteins or any of the antigenic components of the PAG-55 protein fraction can be detected in the blood of the dam at about day 23 through the end of gestation. In a preferable embodiment, the PAG-55 protein fraction are detected from about days 25 to 30 of pregnancy in bovine and other ruminants. The PAG-55 pregnancy test and the methods of the present invention are designed to detect the PAG-55 protein fraction or any of the antigenic components of the PAG-55 protein fraction in the blood, serum, or plasma of the dam. A pregnant cow will also have high progesterone in her blood because she will have a corpus luteum. Thus, pregnant cows will have detectably high levels of PAG-55 protein fraction or any of the antigenic components of the PAG-55 protein fraction and progesterone in their blood, serum, or plasma.

E. Pregnancy Testing in Dairy Cows.

The problem with reproductive management in dairy cattle is that pregnancy detection has previously typically been done 35 to 60 days after breeding. The pregnancy tests of the current invention can be done about 12 to 46 days sooner than the traditional pregnancy testing and only cows with a CL need be injected with PGF. Cows that do not have a CL (and will not respond to PGF) should, instead be injected with GnRH and then treated with PGF at the appropriate time (Fricke, P. M., 2002). By implementing this plan, producers will know which cows are pregnant and inseminate non-pregnant cows within about 28 days of their first insemination. The 20-30 day interval from breeding to pregnancy detection is shorter than current methods and the 28-day interval from first breeding to second breeding for non-pregnant cows is much shorter than the industry average (typically day 45).

Pregnancy testing in dairy cows has usually been done by rectal palpation (manually feeling for an embryo in the uterus). The manual test is typically done 35 to 60 days after breeding. On large dairies, a veterinarian is often employed 100% time to do manual pregnancy testing. The only alternative to manual testing is ultrasound testing. While ultrasound testing can be done at 28 days after breeding, it is not routine because the equipment is expensive and testing takes longer than rectal palpation. The methods of the present invention will be at least as accurate and often more accurate than the traditional rectal palpation as indicated by the results shown in FIG. 2 that compare the accuracy and sensitivities of the palpation method with that of the PAG-55 protein fraction detection methods.

Figure 2A:
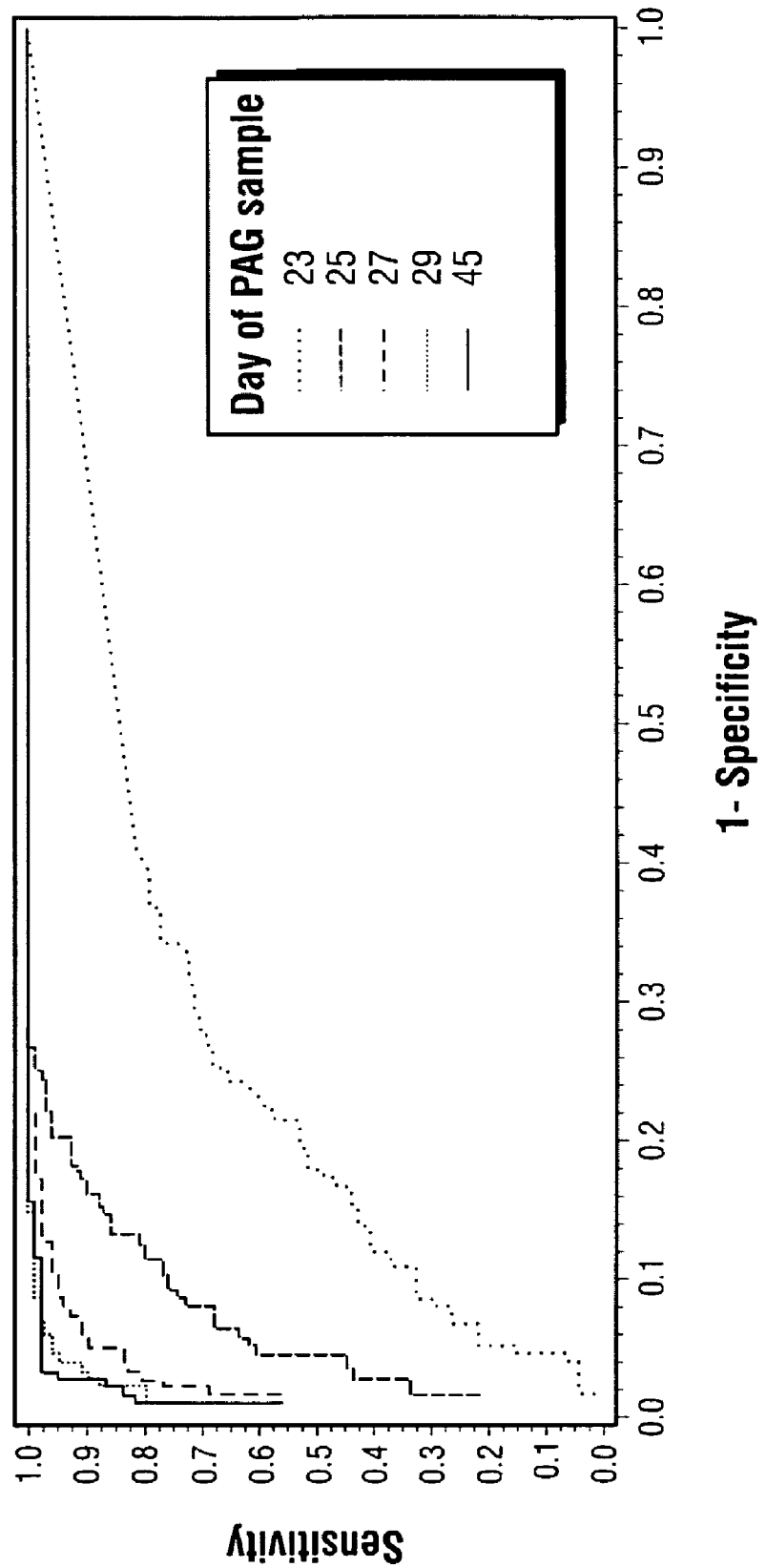
FIGS. 2A and 2B show the accuracy of pregnancy tests using the present invention compared to 45-day palpation results.
Figure 2B:
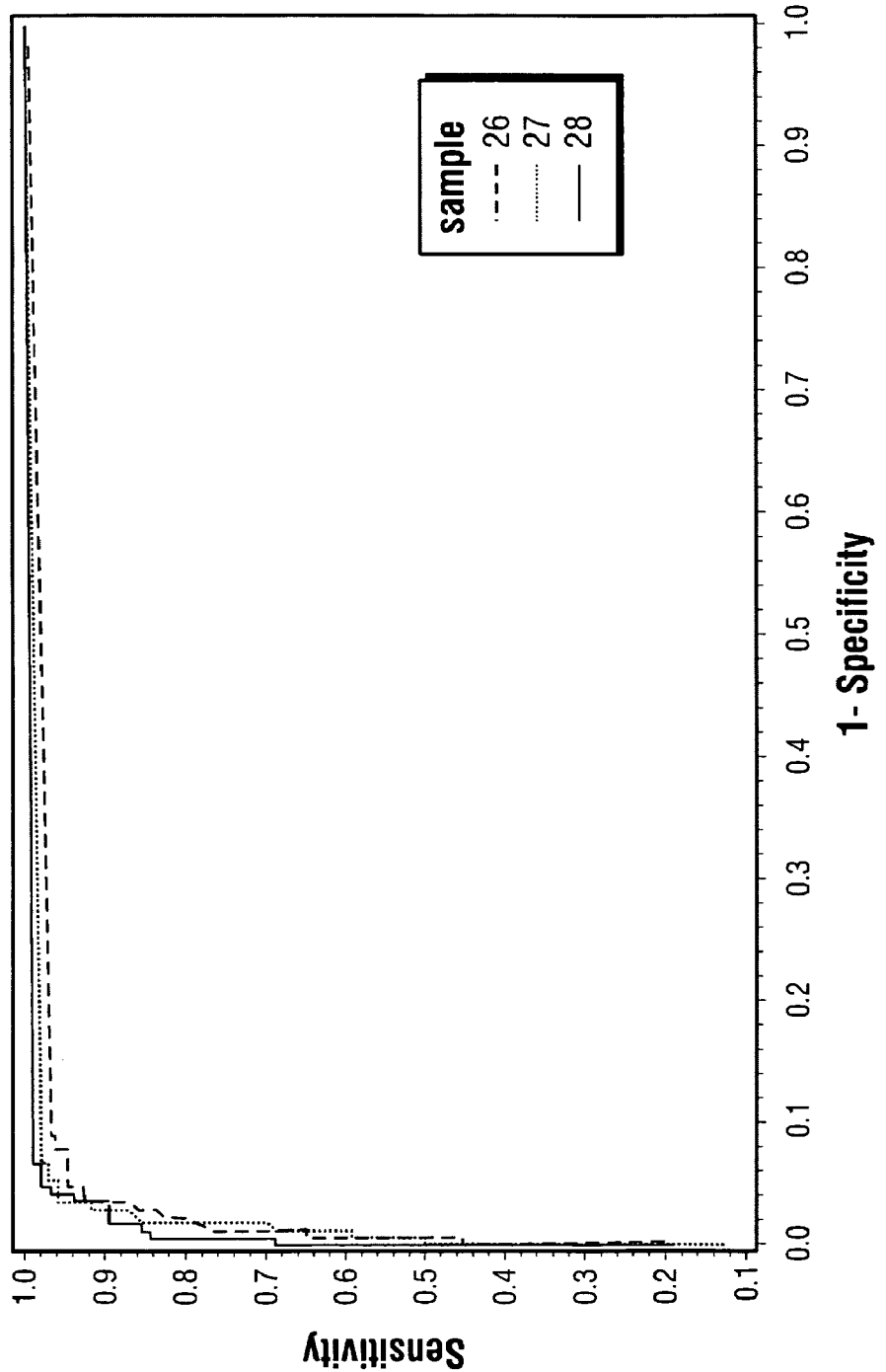

FIGS. 2A-B show the receiver operating curves (ROC) for predicting day-45 palpation results. The curves compare sensitivity and 1 minus the specificity on the days listed. FIG. 2A compares samples collected on days 23, 25, 27, 29, and 45 using the M4 antibody (prepared from day 80 PAG proteins). FIG. 2B compares samples collected on days 26, 27, and 28 using the pooled bleed 6 and 7 of polyclonal anti PAG-55 antibodies of the present invention (which is rabbit anti-bovine PAG).

In Table 2 the PAG cut-offs that maximize sensitivity and specificity at each day of collection are listed. Also shown are the preformances with PAG cut-offs set from 0.00 ng/ml to 1.25 ng/ml.

TABLE 2

| PAG cut-off (ng/ml) | Days post-insemination | Sensitivity (%) | Specificity (%) |
|---|---|---|---|
| Maximize Sens/Spec | | | |
| 0.33 | 26 | 94.8 | 94.7 |
| 0.93 | 27 | 95.9 | 95.8 |
| 0.90 | 28 | 95.8 | 95.8 |
| Set cut-offs | | | |
| 0.00 | 26 | 95.9 | 89.3 |
|  | 27 | 98.0 | 87.5 |
|  | 28 | 99.0 | 88.1 |
| 0.25 | 26 | 94.8 | 93.5 |
|  | 27 | 98.0 | 89.9 |
|  | 28 | 99.0 | 91.0 |
| 0.50 | 26 | 92.8 | 96.4 |
|  | 27 | 96.9 | 92.9 |
|  | 28 | 97.9 | 92.3 |
| 0.75 | 26 | 88.7 | 97.0 |
|  | 27 | 95.9 | 94.0 |
|  | 28 | 96.9 | 95.2 |
| 1.00 | 26 | 83.5 | 97.6 |
|  | 27 | 93.9 | 95.8 |
|  | 28 | 93.8 | 96.4 |
| 1.25 | 26 | 79.4 | 98.2 |
|  | 27 | 87.8 | 97.0 |
|  | 28 | 91.7 | 97.0 |

F. Drugs Used to Manipulate Reproductive Cycles in Dairy Cows.

Dairy cows can be injected with postaglandin $F_{2\alpha}$ (PGF) to regress the corpus luteum and cause estrus. PGF only has effect if the cow has a corpus luteum. Cows that do not have a corpus luteum do not respond to PGF. Instead, dairy cows without a corpus luteum can be injected with gonadotropin-releasing hormone (GnRH) to cause ovulation and the formation of a corpus luteum. One typical method for managing dairy cows without a corpus luteum is to inject GnRH, wait 7 days (allows CL to form), inject PGF and await the cow's next estrus. Both PGF and GnRH are inexpensive and are commonly used in dairy herds (either alone or in combination).

Another approach is to inject GnRH, wait seven days and inject PGF, and then wait two days and inject GnRH (Fricke, P. M., 2002). This protocol (Ovsynch protocol) is popular because cows can be inseminated after the second GnRH without the need for estrus detection.

G. Implementation of Improved Pregnancy Tests in Breeding Programs.

Using the new assays, there are four possible outcomes with respect to the PAG-55 protein fraction or any of the antigenic components of the PAG-55 protein fraction and progesterone results: +/+, +/−, −/+ and −/−. Based on the results, various steps will be desired for implementation of breeding programs. The different possibilities and the likely desired course of action are set forth below in Table 3.

TABLE 3

Reproductive plan implemented 21 days after breeding

| PAG-55 Test Result | Progesterone Test Result | Pregnancy outcome | Farmer action |
|---|---|---|---|
| Positive | Positive | Cow is pregnant | No further action required. |
| Positive | Negative | The embryo underwent early embryonic death and the cow is not pregnant. | Cow does not have a CL (based on low progesterone). Inject GnRH (cause ovulation), wait seven days, inject PGF (regress CL). The producer can breed at estrus or an alternative would be to give another injection of GnRH at 48 hours after PGF to induce ovulation and breed (Fricke, P. M., 2002). |
| Negative | Positive | Cow is not pregnant | Cow has a CL but does not have an embryo. Inject PGF to regress the CL. The farmer can breed at estrus or an alternative would be give another injection of GnRH at 48 hours after PGF to induce ovulation and breed. |
| Negative | Negative | Cow is not pregnant | Cow does not have a CL and does not have an embryo. Inject GnRH, wait seven days, inject PGF. The farmer can breed at estrus or an alternative would be give another injection of GnRH at 48 hours after PGF to induce ovulation and breed. |

H. Types of Assays Used.

According to various embodiments of the present invention the assays to detect the levels of progesterone may be carried out either on biological samples collected on the same day or on biological samples collected on different days, as is convenient and/or most efficacious. In a preferred aspect of this embodiment the assays to determine the levels of PAG-55 protein fraction or any of the antigenic components of the PAG-55 protein fraction and, optionally, the progesterone levels are determined in a sample or samples which are collected on the same day.

In a particularly preferred aspect of this embodiment the assays are ELISA or another antibody based assay (such as a lateral flow technology based strip assay) wherein the antibodies function separately. For example, they may be located at separate positions on the assay device or the assay may utilize one separate device for PAG-55 protein fraction or any of the antigenic components of the PAG-55 protein fraction detection and another for progesterone detection. In an even more preferred aspect of this embodiment of the invention the method for determination of the PAG-55 protein fraction or detection of any of the antigenic components of the PAG-55 protein fraction and progesterone levels in the biological samples comprises the use of one or more "Lateral Flow Assay" device(s) wherein the at least two antigens are detected separately.

According to the instant invention a "Lateral Flow Assay" means an immunochromatographic determination of the presence or absence of an antigen in a biological sample from an animal by: a) combining the sample with a coloring agent-coupled antibody, specific for the antigen; b) allowing the resulting combination to migrate into a first region containing a second antibody to the antigen, which is not coupled to a coloring agent so that the appearance of color in the first region indicates that the antigen is present in the sample; and c) allowing the combination to migrate from the first region into a second region containing an antibody to the first antibody, so that the appearance of color in the second region, together with the absence of color in the first region, serves as a control which indicates that the antibody to the antigen is present, but the antigen is not present; d) allowing the antigen-antibody complex to migrate from the first region into a second region where it is detected by a biosensor or any other electronic detection systems. Typical lateral flow methods are described in U.S. Pat. No. 6,656,744, which is hereby incorporated by reference in its entirety.

IV. The Endometrium and PAG-55 Protein Fraction Samples.

The placenta is the hallmark of the eutherian mammal. Rather than being the most anatomically conserved mammalian organ, however, it arguably is the most diverse (Haig, 1993). Placentation ranges from the invasive hemochorial type, as in the human, where the trophoblast surface is in direct contact with maternal blood, to the epitheliochorial (e.g., pig), where the uterine epithelium is not eroded (Amoroso, 1952). Not only is placental structure highly variable, the polypeptide hormones the placenta produces also vary between species (Haig, 1993; Roberts et al., 1996). For example, no group of mammals other than higher primates possesses a chorionic gonadotrophin homologous to hCG for luteal support in early pregnancy, and only the ruminant ungulates are known to produce Type I interferon as an anti-luteolytic hormone (Roberts et al., 1996).

Placentation in ruminants, such as cattle and sheep, is superficial, relatively noninvasive, and known as synepitheliochorial cotyledonary. "Synepitheliochorial" describes the fetal-maternal syncytium formed by the fusion of trophoblast binucleate cells and uterine epithelial cells, whereas "cotyledonary" describes the gross structure of the placenta and specifically the tufts of villous trophoblast (cotyledons) that insinuate themselves into the crypts of the maternal caruncles. These regions of interdigitated and partially fused fetal cotyledonary and maternal caruncles are the placentomes and are the main sites for nutrient and gas exchange in the placenta. The binucleate cells, which compose about 20% of the surface epithelium (trophectoderm), migrate and fuse with maternal uterine epithelial cells and deliver their secretory products directly to the maternal system. Among the products are the placental lactogens and the pregnancy-associated glycoproteins (PAGs). (Xie et al., 1994, 1996, 1997a, 1997b).

A. Purification of the Proteins

It may be desirable to purify PAG-55 protein fraction or any of the antigenic components of the PAG-55 protein fraction for use as the antigen for the generation of polyclonal or monoclonal antibodies, or for other reasons. Protein purification techniques are well known to those of skill in the art. These techniques involve, at one level, the crude fractionation of the cellular milieu to polypeptide and non-polypeptide fractions. Having separated the polypeptide from other proteins, the polypeptide (or polypeptides) of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. A particularly efficient method of purifying peptides is fast protein liquid chromatography or even HPLC.

Certain aspects of the present invention concern the purification, and in particular embodiments, the substantial purification, of an encoded protein or peptide. The term "purified protein or peptide" as used herein, is intended to refer to a composition, isolatable from other components, wherein the protein or peptide is purified to any degree relative to its naturally-obtainable state. A purified protein or peptide therefore also refers to a protein or peptide, free from the environment in which it may naturally occur. Generally, "purified" will refer to a protein or peptide composition that has been subjected to fractionation to remove various other components, and which composition substantially retains its expressed biological activity.

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. A preferred method for assessing the purity of a fraction is to calculate the specific activity of the fraction, to compare it to the specific activity of the initial extract, and to thus calculate the degree of purity, herein assessed by a "-fold purification number" (i.e., 2-fold, 5-fold, 10-fold, 50-fold, 100-fold, 1000-fold, etc.). The actual units used to represent the amount of activity will, of course, be dependent upon the particular assay technique chosen to follow the purification and whether or not the expressed protein or peptide exhibits a detectable activity.

Various techniques suitable for use in protein purification will be well known to those of skill in the art. These include, for example, precipitation with ammonium sulfate, PEG, antibodies and the like or by heat or acid pH denaturation of contaminating proteins, followed by centrifugation; chromatography steps such as ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified protein or peptide.

There is no general requirement that the protein or peptide always be provided in their most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater "-fold" purification than the same technique utilizing a low pressure chromatography system. Methods exhibiting a lower degree of relative purification may have advantages in total recovery of protein product, or in maintaining the activity of an expressed protein.

It is known that the migration of a polypeptide can vary, sometimes significantly, with different conditions of SDS/PAGE and according to how extensively it is glycosylated (Capaldi et al., 1977). It will therefore be appreciated that under differing electrophoresis conditions, the apparent molecular weights of purified or partially purified expression products may vary.

High Performance Liquid Chromatography (HPLC) is characterized by a very rapid separation with extraordinary resolution of peaks. This is achieved by the use of very fine particles and high pressure to maintain an adequate flow rate. Separation can be accomplished in a matter of minutes, or at most an hour. Moreover, only a very small volume of the sample is needed because the particles are so small and close-packed that the void volume is a very small fraction of the bed volume. Also, the concentration of the sample need not be very great because the bands are so narrow that there is very little dilution of the sample.

Gel chromatography, or molecular sieve chromatography, is a special type of partition chromatography that is based on molecular size. The theory behind gel chromatography is that the column, which is prepared with tiny particles of an inert substance that contain small pores, separates larger molecules from smaller molecules as they pass through or around the pores, depending on their size. As long as the material of which the particles are made does not adsorb the molecules, the sole factor determining rate of flow is the size. Hence, molecules are eluted from the column in decreasing size, so long as the shape is relatively constant. Gel chromatography is unsurpassed for separating molecules of different size because separation is independent of all other factors such as pH, ionic strength, temperature, etc. There also is virtually no adsorption, less zone spreading and the elution volume is related to molecular weight.

Affinity Chromatography is a chromatographic procedure that relies on the specific affinity between a substance to be isolated and a molecule that it can specifically bind to. This is a receptor-ligand type interaction. The column material is synthesized by covalently coupling one of the binding partners to an insoluble matrix. The column material is then able to specifically adsorb the substance from the solution. Elution occurs by changing the conditions to those in which binding will not occur (alter pH, ionic strength, temperature, etc.).

A particular type of affinity chromatography useful in the purification of carbohydrate containing compounds is lectin affinity chromatography. Lectins are a class of substances that bind to a variety of polysaccharides and glycoproteins. Lectins are usually coupled to agarose by cyanogen bromide. Conconavalin A coupled to Sepharose was the first material of this sort to be used and has been widely used in the isolation of polysaccharides and glycoproteins other lectins that have been include lentil lectin, wheat germ agglutinin which has been useful in the purification of N-acetyl glucosaminyl residues and *Helix pomatia* lectin. Lectins themselves are purified using affinity chromatography with carbohydrate ligands. Lactose has been used to purify lectins from castor bean and peanuts; maltose has been useful in extracting lectins from lentils and jack bean; N-acetyl-D galactosamine is used for purifying lectins from soybean; N-acetyl glucosaminyl binds to lectins from wheat germ; D-galactosamine has been used in obtaining lectins from clams and L-fucose will bind to lectins from lotus.

Purification of the PAG-55 proteins of the present invention takes advantage of the general pepstatin binding characteristics of PAGs (Xie et al. 1991). All proteins belonging to aspartic proteinase family of proteins bind strongly to pepstatin, an inhibitor of aspartic proteinases. Pepstatin-affinity chromatography has been successfully used to isolate and characterize the PAG-55 protein fraction of the present invention. Methods involving the use of pepstatin, are known by those skilled in the art, and include those of Huang et al. 1979. Pepstatin A-agarose for chromatography may be obtained commercially from companies such as Sigma Aldrich, St. Louis, Mo. The binding of PAGs to the pepstatin matrix differs depending on the pH. The PAG-55 preparation binds to the pepstatin matrix at an acidic pH.

Generally, the chromatography matrix should be a substance that itself does not adsorb molecules to any significant extent and that has a broad range of chemical, physical and thermal stability. The ligand should be coupled in such a way as to not affect its binding properties. The ligand should also provide relatively tight binding. And it should be possible to elute the substance without destroying the sample or the ligand. One of the most common forms of affinity chromatography is immunoaffinity chromatography. The generation of antibodies that would be suitable for use in accord with the present invention is discussed below.

B. Antigen Compositions

The present invention provides for the use of a PAG-55 protein fraction, proteins, or peptide fragments thereof as antigens for the generation of polyclonal antisera and/or for monoclonal antibodies for use in the detection of any desired antigens of the PAG-55 protein fraction in a biological sample as part of a test for the diagnosis of pregnancy. It is envisioned that certain PAG-55 protein fractions or antigenic components of the PAG-55 protein fraction, or portions thereof, will be coupled, bonded, bound, conjugated or chemically-linked to one or more agents via linkers, polylinkers or derivatized amino acids. This may be performed such that a bispecific or multivalent composition or vaccine is produced. It is further envisioned that the methods used in the preparation of these compositions will be familiar to those of skill in the art and should be suitable for administration to animals, i.e., pharmaceutically acceptable. Preferred agents are the carriers such as keyhole limpet hemocyannin (KLH) or glutathione-S-transferase. Alternatively, PAG-55 proteins could be fractionated using SDS-PAGE, and gel bands corresponding to PAG immunoractivity could be sliced out and used for immunization.

In order to formulate PAG-55 antigens or proteins for immunization, one will generally employ appropriate salts and buffers to render the polypeptides stable. The PAG-55 proteins are mixed with adjuvants and used for immunization. The general protocols used for preparation of antigen/adjuvant mixtures are well known.

The PAG-55 antigen mixed with complete or incomplete adjuvant may be administered intra-dermally, intra-muscularly, intra-peritoneally or according to other general immunization procedures.

V. Generating Antibody Preparations which are Reactive with PAG-55 Proteins and/or Progesterone.

Various embodiments of the present invention will encompass the generation of an antibody preparation wherein the antibodies therein are immunoreactive with PAG-55 protein/s (or any immunoreactive portions thereof) and/or progesterone.

In various aspects of this embodiment of the invention it is contemplated that antibodies (polyclonal, monoclonal or mixtures thereof) specific for the PAG-55 protein fraction, or any of the antigenic components of the PAG-55 protein fraction, or any fragments thereof, may be raised against a PAG-55 protein fraction from any ruminant animal. In a more preferred aspect of this embodiment of the invention the PAG-55 protein fraction, or any of the antigenic components of the PAG-55 protein fraction is from a bovine, ovine, or caprine animal (corresponding to a cow, a sheep, or a goat, respectively). In an even more preferred aspect of this embodiment the PAG-55 protein fraction is isolated from bovine. In one particularly preferred aspect of this embodiment of the invention the bovine PAG-55 protein enriched fraction is used as the antigen to elicit the desired antibodies. The PAG-55 enriched protein fraction may include recombinant constructs encoding the PAG-55 proteins and recombinant DNA techniques, which are well known to those of ordinary skill in the art.

Such an antibody preparation can be a polyclonal or a monoclonal antibody composition, either or both of which are contemplated for use with preferred embodiments of the present invention. An embodiment of the present invention encompasses a mixture of polyclonal antibodies generated using the bovine PAG-55 protein enriched fraction as the antigen to elicit the desired antibodies. Means for preparing and characterizing antibodies are well known in the art (see, e.g., Harlow and Lane, 1988). The preferred embodiment of the present invention is to generate antibodies to the PAG-55 protein fraction and progesterone separately.

Briefly, a polyclonal antibody is prepared by immunizing an animal with an immunogen comprising a peptide/s or polypeptide/s of the present invention and collecting antisera from that immunized animal. A wide range of animal species can be used for the production of antisera. Typically an animal used for production of anti-antisera is a non-human animal including rabbits, mice, rats, hamsters, chickens, pigs, donkeys, or horses. Because of the relatively large blood volume of rabbits, a rabbit is a preferred choice for production of polyclonal antibodies.

Antibodies, both polyclonal and monoclonal, specific for isoforms of antigen may be prepared using conventional immunization techniques, as will be generally known to those of skill in the art. A composition containing desired antigenic epitopes of the compounds of the present invention can be used to immunize one or more experimental animals, such as a rabbit or mouse, which will then proceed to produce specific antibodies against the compounds of the present invention. Polyclonal antisera may be obtained, after allowing time for antibody generation, simply by bleeding the animal and preparing serum samples from the whole blood.

It is proposed that monoclonal antibodies of the present invention will find useful application in standard immunochemical procedures, such as ELISA and Western blot methods and in immunohistochemical procedures such as tissue staining, as well as in other procedures which may utilize antibodies specific for PAG-55 protein fraction-related antigen/s and/or epitopes. Additionally, it is proposed that monoclonal antibodies (mAbs) specific to the particular PAG-55 proteins of different species may be utilized in other useful applications.

In general, both polyclonal and monoclonal antibodies against PAG-55 protein fraction and optionally progesterone, may be used in a variety of embodiments. For example, they may be employed in antibody cloning protocols to obtain cDNAs or genes encoding antibodies to PAG-55 protein fraction and optionally proteins involved in the biosynthesis of progesterone. They may also be used in inhibition studies to analyze the effects of PAG-55 related peptides and optionally progesterone related compounds in cells or animals. Anti-PAG-55 antibodies and optionally antibodies to progesterone pathway enzymes, will also be useful in immunolocalization studies to analyze the distribution of PAG-55 protein fraction and optionally enzymes that participate in progesterone biosynthesis or metabolism during various cellular events, for example, to determine the cellular or tissue-specific distribution of PAG-55 protein fraction or progesterone biosynthesis or metabolism under different points in the cell cycle. A particularly useful application of such antibodies is in purifying native or recombinant PAG-55 protein fraction, for example, using an antibody affinity column. The operation of all such immunological techniques will be known to those of skill in the art in light of the present disclosure.

Means for preparing and characterizing antibodies are well known in the art (see, e.g., Harlow and Lane, 1988; incorporated herein by reference). More specific examples of monoclonal antibody preparation are given in the examples below.

As is well known in the art, a given composition may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimidobencoyl-N-hydroxysuccinimide ester, carbodiimide and bis-biazotized benzidine.

As also is well known in the art, the immunogenicity of a particular immunogen composition can be enhanced by the use of non-specific stimulators of the immune response, known as adjuvants. Exemplary and preferred adjuvants include complete Freund's adjuvant (a non-specific stimulator of the immune response containing killed *Mycobacterium tuberculosis*), incomplete Freund's adjuvants and aluminum hydroxide adjuvant.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster, injection may also be given. The process of boosting and titering is repeated until a suitable titer is achieved. When a desired level of immunogenicity is obtained, the immunized animal can be bled and the serum isolated and stored, and/or the animal can be used to generate mAbs.

MAbs may be readily prepared through use of well-known techniques, such as those exemplified in U.S. Pat. No. 4,196,265, incorporated herein by reference. Typically, this technique involves immunizing a suitable animal with a selected immunogen composition, e.g., a purified or partially purified PAG-55 protein fraction or progesterone. The immunizing composition is administered in a manner effective to stimulate antibody producing cells. Rodents such as mice and rats are preferred animals, however, the use of rabbit, sheep or frog cells is also possible. The use of rats may provide certain advantages (Goding, 1986), but mice are preferred, with the BALB/c mouse being most preferred as this is most routinely used and generally gives a higher percentage of stable fusions.

Following immunization, somatic cells with the potential for producing antibodies, specifically B-lymphocytes (B-cells), are selected for use in the monoclonal antibody generating protocol. These cells may be obtained from biopsied spleens, tonsils or lymph nodes, or from a peripheral blood sample. Spleen cells and peripheral blood cells are preferred, the former because they are a rich source of antibody-producing cells that are in the dividing plasmoblast stage, and the latter because peripheral blood is easily accessible. Often, a panel of animals will have been immunized and the spleen of animal with the highest antibody titer will be removed and the spleen lymphocytes obtained by homogenizing the spleen with a syringe. Typically, a spleen from an immunized mouse contains approximately $5 \times 10^7$ to $2 \times 10^8$ lymphocytes.

The antibody-producing B lymphocytes from the immunized animal are then fused with cells of an immortal myeloma cell, generally one of the same species as the animal that was immunized. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas).

Any one of a number of myeloma cells may be used, as are known to those of skill in the art (Goding, 1986; Campbell, 1984). For example, where the immunized animal is a mouse, one may use P3-X63/Ag8, P3-X63-Ag8.653, NS1/1.Ag 4 1, Sp210-Ag14, FO, NSO/U, MPC-11, MPC11-X45-GTG 1.7 and S194/5XX0 Bul; for rats, one may use R210.RCY3, Y3-Ag 1.2.3, IR983F and 4B210; and U-266, GM1500-GRG2, LICR-LON-HMy2 and UC729-6 are all useful in connection with cell fusions.

Methods for generating hybrids of antibody-producing spleen or lymph node cells and myeloma cells usually comprise mixing somatic cells with myeloma cells in a 2:1 ratio, though the ratio may vary from about 20:1 to about 1:1, respectively, in the presence of an agent or agents (chemical or electrical) that promote the fusion of cell membranes. Fusion methods using Sendai virus have been described (Kohler and Milstein, 1975; 1976), and those using polyethylene glycol (PEG), such as 37% (v/v) PEG, by Gefter et al., (1977). The use of electrically induced fusion methods is also appropriate (Goding, 1986).

Fusion procedures usually produce viable hybrids at low frequencies, around $1 \times 10^{-6}$ to $1 \times 10^{-8}$. However, this does not pose a problem, as the viable, fused hybrids are differentiated from the parental, unfused cells (particularly the unfused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

The preferred selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B-cells can operate this pathway, but they have a limited life span in culture and generally die within about two weeks. Therefore, the only cells that can survive in the selective media are those hybrids formed from myeloma and B-cells.

This culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays, dot immunobinding assays, and the like.

The selected hybridomas would then be serially diluted and cloned into individual antibody-producing cell lines, which clones can then be propagated indefinitely to provide mAbs. The cell lines may be exploited for mAb production in two basic ways. A sample of the hybridoma can be injected (often into the peritoneal cavity) into a histocompatible animal of the type that was used to provide the somatic and myeloma cells for the original fusion. The injected animal develops tumors secreting the specific monoclonal antibody produced by the fused cell hybrid. The body fluids of the animal, such as serum or ascites fluid, can then be tapped to provide mAbs in high concentration. The individual cell lines could also be cultured in vitro, where the mAbs are naturally secreted into the culture medium from which they can be readily obtained in high concentrations. mAbs produced by either means may be further purified, if desired, using filtration, centrifugation and various chromatographic methods such as HPLC or affinity chromatography.

A. Development of a Polyclonal PAG-55 Immunoassay.

The following section describes the development of a polyclonal antibody-based assay for detecting the PAG-55 protein fraction. Antigen and antibody proteins may be prepared and isolated by any means known to those of ordinary skill in the art. This assay may be used to determine the feasibility of detecting PAG-55 protein fraction or any antigenic components of the PAG-55 protein fraction during early pregnancy using various polyclonal antibodies.

An immunoassay developed with antibodies reactive to full-length, native, immunogenic components of PAG-55 protein fraction, or recombinant bovine PAG-55 protein fraction will detect a PAG-55 protein fraction present in a biological sample such as serum, plasma, saliva, urine, or blood with high specificity and sensitivity. A PAG-55 specific immunoassay, may be developed by first raising an antibody to purified, acidic PAG-55 fractions, such as those isolated from the day 55 to about day 60 bovine conceptus. Alternatively, certain purified recombinant PAG-55 antigens may be produced in yeast or bacteria, and may be used as the antigen.

Antibodies may be generated in rabbits according to any standard protocol, typically using purified PAG-55 protein fraction in Freund's complete adjuvant. After a two-week interval these rabbits may be boosted with the antigen and incomplete adjuvant. The rabbits can then be boosted every two weeks until sufficient antisera were collected and stored at −20° C. Polyclonal antibodies can then be affinity purified using protein A chromatography and dialyzed in PBS. Purified antibodies are then aliquoted and stored at −20° C.

B. Design of a Combination PAG-55/Progesterone Early Pregnancy Test and Expected Results.

An assay format analyzing both progesterone and PAG-55 protein fraction levels may be designed. Additionally, due to a high incidence of early embryonic loss in cattle, a combined detection of both a pregnancy induced protein such as PAG-55 and a maternal component such as progesterone would more accurately diagnose the pregnancy status of an animal than would testing for only one analyte. A series of designated PAG-55 protein fraction and progesterone cutoff levels for pregnancy determination based on given concentrations of PAG-55 and progesterone can be formulated. For each day post insemination a series of analyses may be done to determine the appropriate cut off levels for serum (or other sample) levels of PAG-55 protein fraction in cows.

For example, studies may be done that determine the serum levels of PAG-55 protein fraction and progesterone in a statistically significant number of cows on the days following artificial insemination or non-insemination as control. By charting the serum PAG-55 protein fraction and progesterone levels in those cattle, subsequently identified as being pregnant by another method (such as rectal palpation or sonography) a standard may be statistically calculated which provides a baseline level of PAG-55 protein fraction and progesterone, below which a cow should be considered non-pregnant and above which a cow should be considered pregnant.

Using these values, a test can be made to provide the appropriate indication of a positive result for PAG-55 protein fraction and, optionally, progesterone only when the levels of those compounds in the biological sample are above the determined level.

The same data may also be used to determine the optimal window to allow for the early detection of pregnancy which provides both acceptable sensitivity and accuracy and diagnosis early enough to allow re-breeding so as to minimize the time the cow is open.

For example, two cutoff ranges (3 ng/ml and 2 ng/ml) have been determined for progesterone. The cutoff ranges were selected based on: a) pregnancy history of the cows, and b) progesterone levels during estrus cycle and pregnancy in cows.

It is expected that the results achieved by the method described above will provide a combination PAG-55/progesterone pregnancy detection test that is both accurate and sensitive. Furthermore, this test will provide critical information allowing herd managers to optimize profits by minimizing the amount of time that herd animals remain open.

C. Diagnosis of Pregnancy/Non-pregnancy in a Bovine Suspected of Being Pregnant.

Antibodies may be raised respectively against PAG-55 antigens and progesterone. These antibodies may then be employed to prepare a kit comprising, inter alia, the components necessary to provide sandwich-type ELISA assays or to provide lateral flow technology based test strips for detecting the presence of the PAG-55 protein fraction and optionally, progesterone in a biological sample.

A typical immunodetection strip may have at least one arrow near the top portion of the strip to indicate which end of the strip to place in the media (e.g. blood). The blood is typically pulled through the strip by capillary action. A typical test strip will have a first indicator zone (a test line), which if there is a line present in this first indicator zone, indicates that the animal is pregnant (sandwich-type assay) or no line in the indicator zone (a competitive type assay) if the animal is pregnant. A typical test strip may also have a second line, (lower line) that is a control line that indicates that the test has run properly. It will typically be the case that all strips will exhibit a positive reaction with the control line, which functions as a positive control.

The pregnancy status of a bovine may then be determined by collecting a biological sample after natural breeding or artificial insemination. The biological sample, such as serum taken from day 23 through the end of gestation, can then be analyzed to determine the levels of PAG-55 protein fraction or any antigenic component thereof and progesterone in the sample. Threshold levels can be individually established which will be determined to be a "positive" result (a positive result meaning that the animal is pregnant) for PAG-55 protein fraction and progesterone ELISA assays. According to one aspect of the present invention it has been determined that for certain applications a suitable cutoff level for designation as a "positive result" for PAG-55 protein fraction is any detectable level above zero ng/ml or higher, and for progesterone the level is about 2 ng/ml or higher.

D. Resynchronization of Dairy Cows and Heifers After PAG-55 and Progesterone Detection for Pregnancy Diagnosis.

The following is a method for re-breeding cows and heifers that are diagnosed as not pregnant after a PAG-55/progesterone test. Generally, cattle are tested for PAG-55/progesterone 16 to 28 days after natural breeding or artificial insemination and are diagnosed pregnant or non-pregnant. The resynchronization method is implemented on non-pregnant cows 0 to 2 days after the PAG-55/progesterone test. Animals are treated in the following sequence: (i) inject prostaglandin $F_{2\alpha}$ ($PGF_{2\alpha}$; a hormone causing regression of the corpus luteum); (ii) wait two days, inject gonadotropin releasing hormone (GnRH; a hormone causing ovulation); (iii) wait 0 to 8 hours; (iv) inseminate artificially.

Dairy cows and heifers are tested for reactivity with PAG-55 polyclonal or monoclonal antibodies 16 to 28 days after first artificial insemination. Cattle diagnosed not pregnant are treated with 5 mL Lutalyse (25 mg $PGF_{2\alpha}$), two days later were treated with 2 mL Cystorelin (100 µg GnRH), and are inseminated 0 to 8 hours after GnRH. The resynchronization treatment is administered 0 to 2 days after the PAG-55 test (16 to 30 days after first insemination). Pregnancy is determined 30 to 60 days after insemination.

VI. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Isolation and Characterization of PAG-55 Enriched Protein Fraction

The following flowchart describes the purification of acidic PAG-55 fraction, enriched for early PAGs, isolated from day 55-60 bovine cotyledonary tissue (which is a descriptive term for the gross structure of the placenta and specifically the tufts of villous trophoblast (cotyledons) that insinuate themselves into the crypts of the maternal caruncles). Shown below are steps of the purification and various buffer compositions.

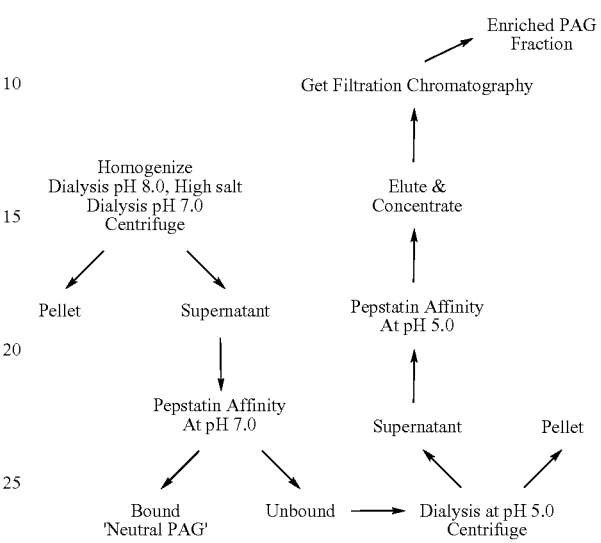

Generally, the above purification process utilizes the pepstatin binding characteristic of PAGs. Based upon the pepstatin binding characteristics of PAGs at various different pH's, PAGs can be fractionated, or separated into three categories: neutral PAGs (PAGs binding to pepstatin at neutral pH), acidic PAGs (PAGs binding to pepstatin in acidic pH, and basic PAGs (PAGs binding to pepstatin in basic pH). The fraction most suitable for use in pregnancy tests of the present invention is the acidic PAG fraction, referred to herein as the "acidic PAG enriched fraction".

A. Tissue Collection, Purification, and Homogenization.

Bovine cotyledonary tissue was harvested from day 55 to 60 placenta and was stored frozen at –20° C. until the purification procedure was carried out. Typically, a purification procedure will start with about 15-20 grams of tissue material, isolated from about three to four animals that are pooled. Typical yields of cotyledon tissue range from about 2 grams to about 10 grams per animal.

1. Purification. A 20% solution of cotyledonary tissue was prepared (i.e., add 20 ml tissue to 80 ml of buffer) in homogenization buffer (10 mM phosphate, pH 7.0; 150 mM NaCl; 5 mM EDTA, 0.2 mM PMSF (phenyl methyl sulfonyl fluoride), 0.02% w/v $NaN_3$) and homogenized using a Polytron® homogenizer in a volume of 25-30 ml aliquots in a 50 ml tube on ice. The tissue suspension was homogenized for one minute at 15,000 rpm and then an additional two minutes at 20,000 rpm. The homogenate was then poured into a separate container and the process was repeated until all of the suspension was complete. The homogenate was then centrifuged (in 35 ml screw-capped tubes) in a Sorvall® SS34 rotor at 15,000 rpm at 4° C. for 30 minutes.

B. pH 8 and pH 7 Dialysis of Homogenate.

The supernatant obtained after the above-described centrifugation was dialyzed in a 50 kD molecular weight cut-off dialysis bag or other suitable tubing, against a pH 8.0 dialysis buffer (20 mM Tris, pH 8.0, 1 M NaCl, 1 mM EDTA, 0.2 mM PMSF, 0.02% $NaN_3$ and 0.1 mM 2-mercaptoethanol) for 12-16 hours, changing the buffer every 4-6 hours (typically 3 total buffer changes with pH 8 buffer). After this step (after the third dialysis pH 8 buffer change), the dialysis of the homogenate continued with pH 7.0 buffer (20 mM Tris, (pH 7.0), 0.15 M NaCl, 1 mM EDTA, 0.2 mM PMSF, 0.02% $NaN_3$ and 0.1 mM 2-mercaptoethanol) for an additional 12-16 hours, changing the buffer about every 4 hours—resulting in 3 buffer changes. All dialysis/buffer steps were performed at 4° C.

C. Neutral Pepstatin Binding.

After the dialysis at pH 7.0 was completed, the dialysate was transferred into centrifuge tubes and centrifuged at 15,000×g at 4° C. for 30 minutes. The supernatant was poured into a 250 ml centrifuge bottle containing 50 ml of pre-equilibrated pepstatin agarose resin (which is in a buffer of: 20 mM Tris, pH 7.0, 0.15 M NaCl, 1 mM EDTA, 0.2 mM PMSF, 0.02% $NaN_3$ and 0.1 mM 2-mercaptoethanol). The centrifuge bottle was placed in a rotator and the resin slurry was rotated at 4° C., at a speed setting of about 10-20 rpm, for 16 to 20 hours.

D. Pepstatin-Agarose Binding at Neutral pH.

After the binding step above, the pepstatin agarose resin slurry from the centrifuge bottle was transferred to a column (2.5 cm×15 cm) at 4° C. with an outlet open to collect the flow-through solution into a clean 500 ml glass beaker. The column was washed with 5 bed volumes of the same buffer (20 mM Tris, pH 7.0, 0.15 M NaCl, 1 mM EDTA, 0.2 mM PMSF, 0.02% $NaN_3$ and 0.1 mM 2-mercaptoethanol). The washings were pooled with flow-through solution in the 500 ml beaker. The combined column flow-throw and wash solution were then dialyzed against pH 5.0 buffer (20 mM citrate, pH 5.0, 0.15 M NaCl, 1 mM EDTA, 0.2 mM PMSF, 0.02% $NaN_3$ and 0.1 mM 2-mercaptoethanol) for about 12-16 hours at 4° C. with 3 buffer changes. After the dialysis, the dialysate solution was transferred into screw-capped centrifuge bottles and centrifuged at 15,000×g for 30 minutes at 4° C.

E. Pepstatin-Agarose Binding at Acidic pH.

The supernatant from step D above, was then transferred into a 250 ml screw-capped centrifuge bottle containing 50 ml of pre-equilibrated pepstatin-agarose resin in pH 5.0 buffer (20 mM citrate, pH 5.0, 0.15 M NaCl, 1 mM EDTA, 0.2 mM PMSF, 0.02% $NaN_3$ and 0.1 mM 2-mercaptoethanol). The centrifuge bottle with the pepstatin agarose resin slurry was placed in a rotator and rotated at 4° C., with a speed setting of about 10-20 rpm, for about 16 to 20 hours. After this step, the pepstatin-agarose resin (which is acidic) was transferred into a column (2.5 cm×20 cm) and washed with pH 5 wash buffer (20 mM citrate, pH 5.0, 1 M NaCl, 1 mM EDTA, 0.2 mM PMSF, 0.02% $NaN_3$, 0.1 mM 2-mercaptoethanol and 0.1% Triton X-100) until the column flow-through optical density (absorbance) at $OD_{280}$ was ≦0.001, then the column was eluted with pH 9.5 elution buffer (20 mM Tris, pH 9.5, 1 M NaCl, 1 mM EDTA, 0.2 mM PMSF, 0.02% $NaN_3$, 0.1 mM 2-mercaptoethanol and 0.1% Triton X-100). Forty 2 ml fractions were collected into tubes containing 0.2 ml of 1M Tris, pH 7.0.

F. Pooling and Concentration of Acidic PAG-55 Eluates.

The eluted fractions were analyzed by immuno dot-blot analysis with PAG-55 polyclonal antibodies. Briefly, 8 µl of each eluate fraction were mixed with 1 µl of SDS and spotted onto a nitrocellulose filter. After blocking with 5% non-fat dry milk, the filter was incubated with PAG polyclonal antibodies for one hour at room temperature. After washing the filter, the blot was incubated with anti-rabbit antibody conjugated with alkaline phosphatase. After washing, the blot was developed with BCIP/NBT (5-bromo-4-chloro-3-indolyl phosphate/nitroblue tertrazolium) color development substrate (such as found in alkaline phosphatase chromogen kits) for approximately 15 minutes or long enough to see the eluate spots. The color development substrate solution was poured off into an appropriate container for disposal.

PAG immuno-reactive fractions from the first elution peak are pooled and concentrated with phosphate buffered saline in Millipore Centricon® Plus 30 kD MWCO concentrators to a volume of 1.0 ml. The concentrated fraction was stored frozen at −20° C. until used for gel filtration chromatography.

G. Gel Filtration Chromatography of Acidic PAG-55 Eluates.

Figure 4:
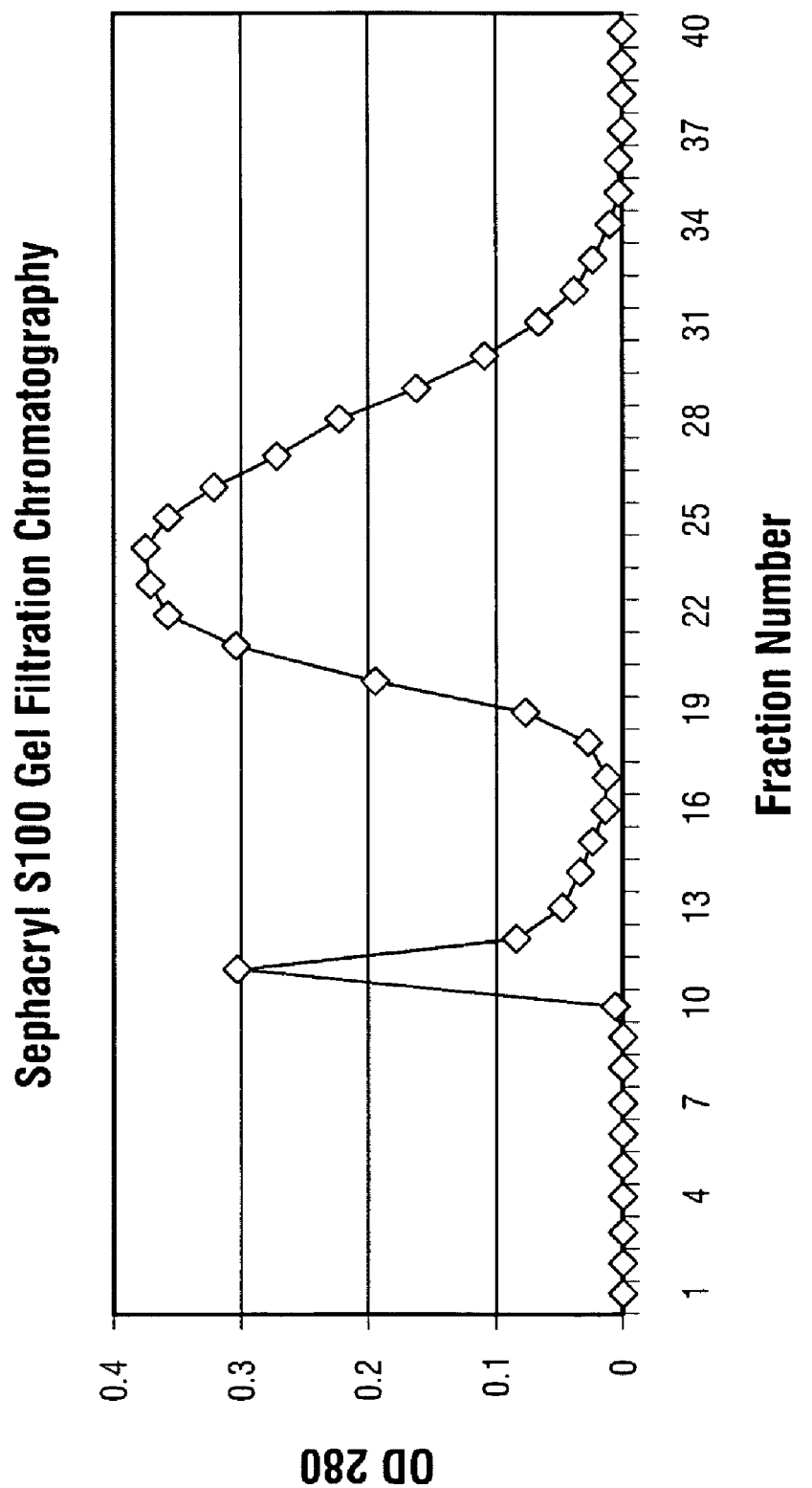
FIG. 4 shows fractionation of PAG-55 protein fraction with Sephacryl gel filtration chromatography.

The pepstatin-agarose eluted acidic PAG-55 fraction was then fractionated with gel filtration chromatography by using a 40 cm×1.5 cm column of Sephacryl S-100 resin pre-equilibrated with PBS. The gel filtration column was loaded with about 1 mg of concentrated acidic PAG-55 purified protein fraction purified from the eluted acidic pepstatin column as described in part F above. The Sephacryl column was eluted with phosphate buffered saline at a flow rate of about 0.25 ml to 0.5 ml/min. Fifty 1 ml-fractions were collected and the $OD_{280}$ of each fraction was checked, recorded, and plotted. FIG. 4 shows a typical elution profile of the concentrated acidic PAG-55 protein fraction purified from the acidic pepstatin column. Based on analysis of the fractions, the first protein peak and the fractions between the first and second peak were pooled and concentrated in PBS. The first protein peak fractions of the acidic PAG-55 fraction are shown in FIG. 4. In FIG. 4, fractions 9-18 were pooled and concentrated to about 1 mg/ml and this concentrated material is referred to as the PAG-55 protein fraction or antigen/s. The concentrated material, also referred to as the acidic PAG-55 fraction, is stored frozen at −20° C. until use. This material was also subjected to electrophoretic analysis with 10% polyacrylamide gels and Western blot analysis.

Figure 1B:
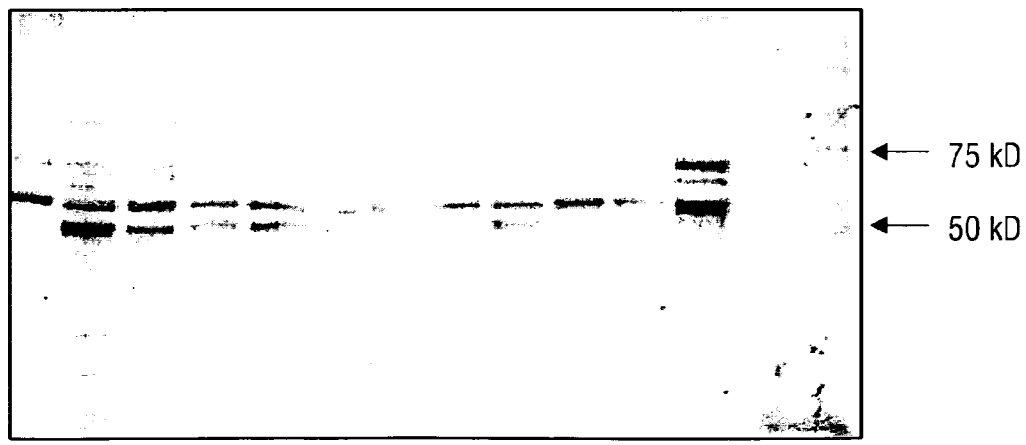

FIG. 1 shows SDS-PAGE and Western blot analysis of the isolated day 55 PAG antigen fraction. FIG. 1A is a silver stained gel of day 55 antigen from multiple purification batches (lanes 1-10), day 55 antigen stored at 4° C. (lane 11), day 80 PAG antigen (lane 12), BSA (lane 13) and molecular weight markers (lane 14). FIG. 1B is a Western blot of the same gel shown in FIG. 1A that has been developed with polyclonal antibody raised against day 80 PAG antigen. Note that the day 55 PAG antigen fraction shows immunoreactivity at 46 kD, 55 kD, and 67-73 kD). In contrast, the day 80 PAG antigen fraction shows distinct immunoreactive bands at 55 kD, 67 kD and 73 kD.

FIG. 5 shows a silver stained gel of 'PAG antigen' purified from day 55 bovine placenta in lane 1. Lane 3 shows the Western blot analysis of PAG antigen with anti-PAG antibody. The material undergoes proteolysis when stored at 4° C. (lanes 2 & 4, lane 5 are the molecular weight markers); thus, the purified material should be stored frozen at −20° C.

The purified acidic PAG-55 fraction is enriched for early PAGs. It is estimated that about 10% to 20% of the total proteins from this purified fraction correspond to PAG proteins. This preparation was used for immunizing animals as described below.

H. 2-Dimensional Gel Electrophoretic Analysis of Day 55 PAG Antigen.

The purified, acidic 55 PAG antigen fraction was subjected to 2-D gel analysis and Western blot analysis with polyclonal antibodies raised against PAG-55 protein fraction. The immunoreactive spots labeled 1, 2, and 3 in FIG. 6, were cut out and subjected to peptide mass finger printing (amino acid sequencing by mass spectroscopy). Spots corresponding to PAG immunoreactivity are indicated by circles.

Peptide sequencing of spots 1 and 2 identified peptide fragments that correspond to PAG-6 (also described in FIG. 8A):

```
PAG-6 Peptide sequences:
IGDLVSTDQPFGLCLK              (SEQ ID NO:3)

TFSGAFPIFDK                   (SEQ ID NO:4)

NEGAISEPVFAFYLSK              (SEQ ID NO:5)

DKQEGSVVMFGGVDHR              (SEQ ID NO:6)

ALVDTGTSDIVGPSTLVNNIWK        (SEQ ID NO:7)

YFSVFDR                       (SEQ ID NO:8)
```

Peptide sequencing of spot 3 yielded a mixture of peptides corresponding to:

```
PAG-4 Peptide sequences:
TFSITYGSGR                    (SEQ ID NO:12)

VPGQAYILK                     (SEQ ID NO:13)

YFSVFDR                       (SEQ ID NO:14)

PAG-9 Peptide sequences:
NQGAISEPVFAFYLSK              (SEQ ID NO:27)

RYFSVFDR                      (SEQ ID NO:28)

PAG-16 Peptide sequences:
LNYPNLSCSGAIPIFDK             (SEQ ID NO:19)

EGSVVMFGGVDHR                 (SEQ ID NO:20)

GELNWVPLIR                    (SEQ ID NO:21)

YFSVFDR                       (SEQ ID NO:22)

PAG-18 Peptide sequences:
NQGAISEPVFAFYLSK              (SEQ ID NO:9)

AVVDTGTSLIEGPR                (SEQ ID NO:10)

RYFSVFDR                      (SEQ ID NO:11)

PAG-19 Peptide sequences:
TFSITYGSGR                    (SEQ ID NO:23)

NQGAISEPVFAFYLSK              (SEQ ID NO:24)

EGSVVMFGGVDHR                 (SEQ ID NO:25)

YFSVFDR                       (SEQ ID NO:26)

a new PAG (MonPAG)
(also described in FIG. 8A-B)
Peptide sequences:
ISSSGAIPIFDK                  (SEQ ID NO:15)

EGSVVMFGGVDHR                 (SEQ ID NO:16)

NQGAISEPVFAFYFSK              (SEQ ID NO:17)

IGDLVSTDQPFGLSTAEYGFK.        (SEQ ID NO:18)
```

The peptide sequences were analyzed by PEAKS™ protein analysis software (Bioinformatics Solutions, Inc., Ontario, Canada). The peptide mass (Mz), charge of the peptide, calculated molecular weight, % confidence score in the sequencing, amino acid start and end position of consensus PAG sequences for the spots 1, 2 and 3 are described FIGS. 8A and 8B. It appears that a mixture of PAG-6, PAG-4, PAG-9, PAG-16, PAG-18, PAG-19 and the new Mon PAG make up the acidic PAG-55 fraction and that any combination of these proteins, and preferably all of them will be useful for generating polyclonal antibodies for the early detection of pregnancy.

The partial sequence information of a new PAG present in the spot 3, called Mon PAG is shown in FIG. 7A-B. A partial sequence of the Mon PAG spot by peptide mass finger printing (sequencing) identified a bovine EST sequence (BP112041) in the public sequence database. This bovine EST sequence corresponding to the Mon PAG protein has accession number BP112041 (SEQ ID NO:1). The sequence was published as a part of large number of Bovine EST sequences in Molecular Reproduction and Development 65: 9-18, 2003, which is incorporated by reference herein. The predicted amino acid sequence of this EST is shown in FIG. 7B (SEQ ID NO:2). The amino acid residues in bold and underlined were identified by peptide finger printing (sequencing) of day 55 PAG antigen following 2D-gel analysis.

Example 2

Generation of Polyclonal Antibodies Immunoreactive with PAG-55 Enriched Protein Fraction 10 rabbits were immunized with day 55-60 acidic PAG fraction by using standard immunization protocols (i.e. with an adjuvant). The monthly bleeds were checked for antibody titer and IgG purification. The purified IgG fraction from all 10 rabbits was used for developing the PAG-55 ELISA. A test panel of bovine plasma samples (37 pregnant and 24 open cows) from day 28 post insemination was used to determine the sensitivity (ability to detect pregnant cows) and specificity (ability to detect open cows) in a PAG-55 ELISA optimized with antibodies from each rabbit. The test panel results with IgG fraction from the 7$^{th}$ bleed for five rabbits are shown in Table 4.

TABLE 4

| | PAG-55 ELISA RESULTS | | | | |
|---|---|---|---|---|---|
| | #368 | #369 | #370 | #371 | #375 |
| Sensitivity (%) | 89 | 100 | 100 | 100 | 76.5 |
| Specificity (%) | 91 | 100 | 100 | 96 | 86.5 |
| Cut-off (ng/ml) | 0.8 | 0 | 1.5 | 1.0 | 0.9 |

The Table 4 results show that rabbit IgGs from test samples #368, #369, #370, and #371 could be used successfully to detect pregnancy in cows at day 28 of gestation accurately.

Figure 3A:
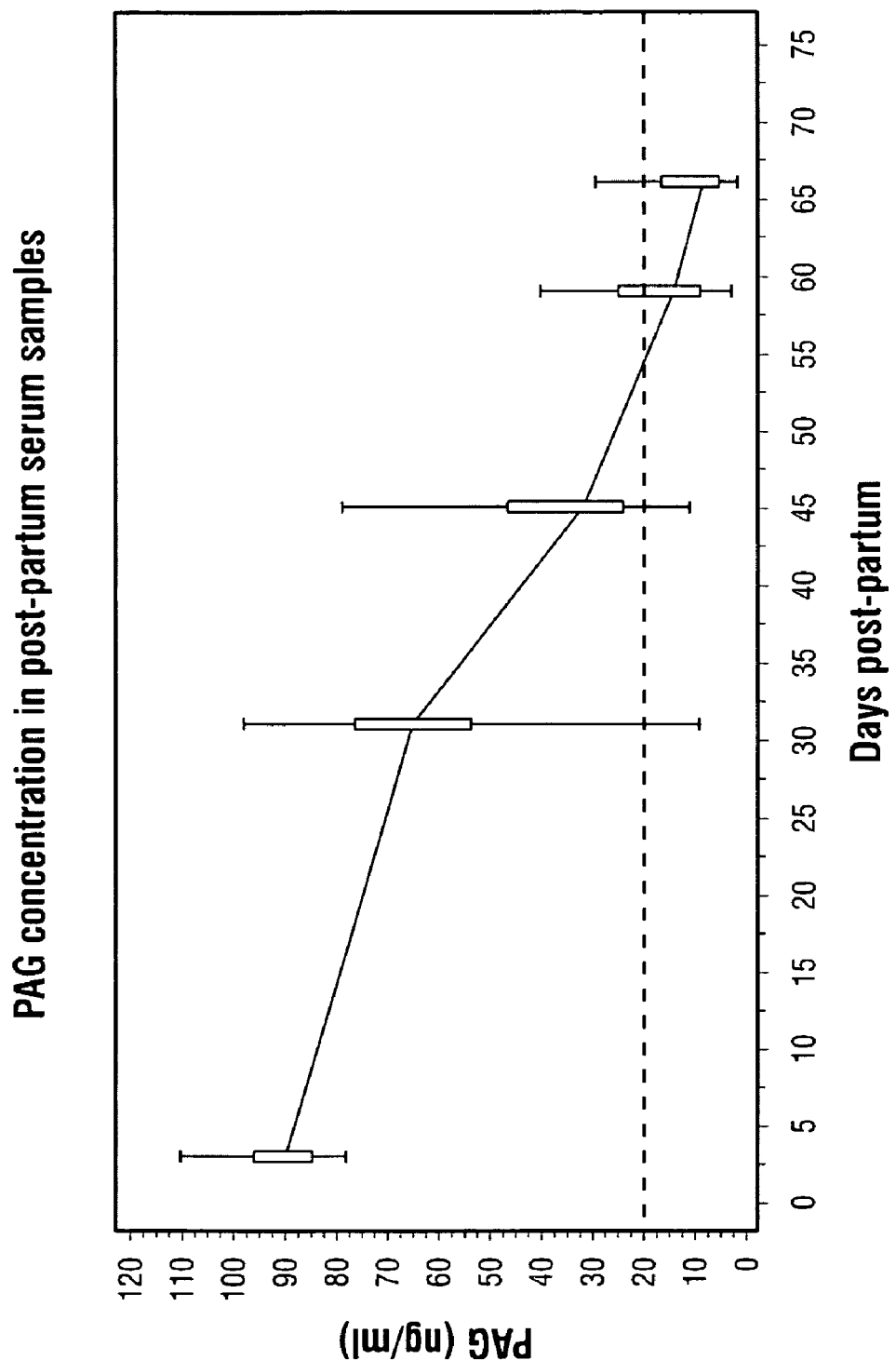
FIG. 3B shows the rapid return of PAG-55 protein fraction to background levels in post partum serum samples, when compared to the post-partum PAG detected by the UMC-M4 antibody in FIG. 3A.
Figure 3B:
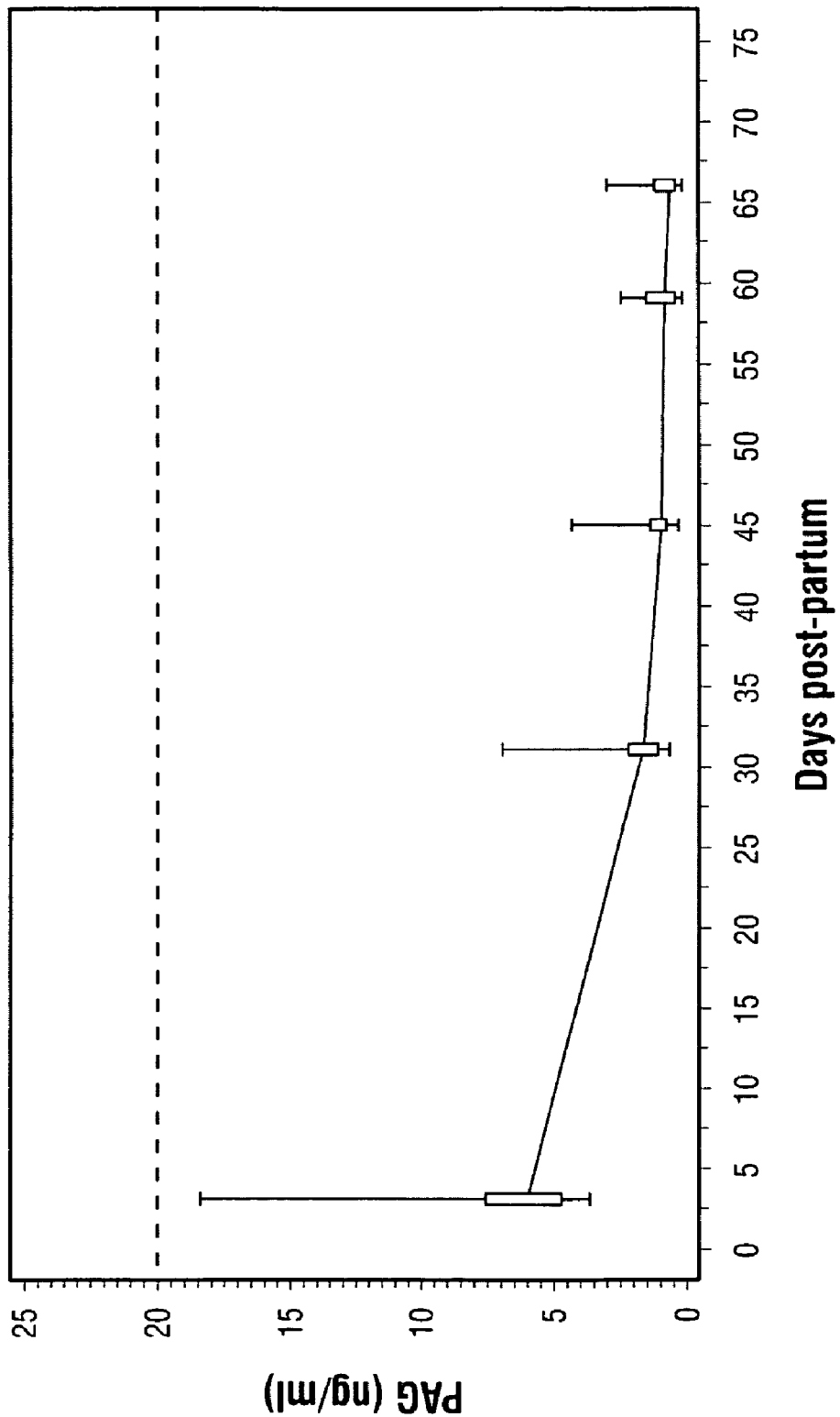

The 4$^{th}$ bleed IgG assay from #368 was used for determining the post-partum immuno-reactivity in 40 cows up to 10 weeks postpartum. The results as shown in FIG. 3B illustrate that the plasma values for PAG-55 antigens, as detected by antibody #368 (described in Table 4) were below 2 ng/ml by day 45 post-partum. The same postpartum samples were also assayed with the UMC-M4 antibody for comparison. The UMC-M4 antibodies were generated to acidic PAG proteins that were isolated from day 80-100 conceptuses. The results showed that the late PAG proteins (day 80-100 acidic PAG antigen), detected by the UMC-M4 antibody were present at the level of >20 ng/ml at day 45 post partum, and over 10 ng/ml at day 65 post-partum (FIG. 3A). Thus, PAG-55 proteins exhibit a distinctly different and more rapid return to the baseline level of <2 ng/ml by about day 45 post partum and represent an improvement for early pregnancy detection.

Example 3

Comparing Whole, Non-Clotted Blood to Non-Centrifuged, Clotted Blood for Use in PAG-Based Pregnancy Tests for Cows Using Lateral Flow Technology Whole blood was collected from thirteen Holstein cows from the coccygeal vein. Blood was collected into either a 4 ml Vacutainer® (Becton Dickinson) serum separator tube (SST tube, containing at least one clot activator or a gel and clot activator), or into a 10 ml Vacutainer® plasma tube containing $K_3$ EDTA. Plasma tubes were kept on ice while the serum separator tubes were maintained at room temperature. Clot activators include any agent that promotes clot formation including, but not limited to thrombin, phospholipids, kaolin (a clay material), micronized silica (e.g. polysiloxane), and calcium. Other factors that could be added to the collection tubes include platelet agonists, such as collagen or the thrombin receptor agonist peptide, SFLLRN, that would be expected to significantly accelerate the clotting of native whole blood and to accelerate both the onset and completion of clot formation (i.e. fibrin gel formation).

Figure 10:
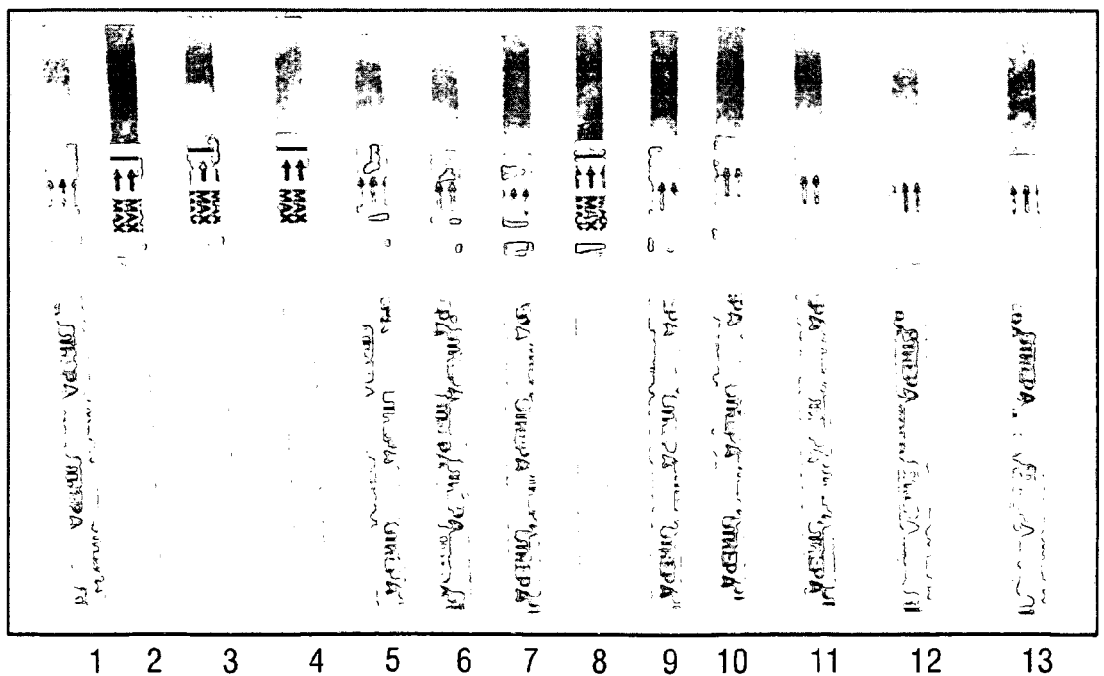
FIG. 10 shows test strips containing PAG-55 antibodies exposed to unclotted blood samples.

To test the accuracy of using whole blood in an on-farm PAG-55 based immunodetection assay, a 400 µl sample of whole blood was removed from the 10 ml Vacutainer® plasma tube containing $K_3$ EDTA and placed in an ~1 ml microfuge tube. Anti-bovine PAG-55 lateral flow test strips designed to detect pregnancy in bovines were placed in the whole blood samples, such that the strips were in fluid communication with the blood sample, and were allowed to develop for approximately 5 minutes. The results obtained showed reactive bands that were smeared and not easy to read or interpret with the naked eye, as shown in FIG. 10, which illustrates test strips exposed to whole, unclotted blood samples. The poor results obtained using the whole, unclotted blood sample in the plasma tube with $K_3$ EDTA indicated that red blood cells, lytic products, or hemolyzed blood from the sample were drawn into the test, or "reading" area of the lateral flow strip. This red blood cell material causes "smears" and interferes with the test result, making the interpretation of results read within the test area difficult, or impossible. FIG. 10, Lanes 1, 5, 6, 7, 8, and 11 all contain red blood cells covering the "test line," making them impossible to read.

Figure 9:
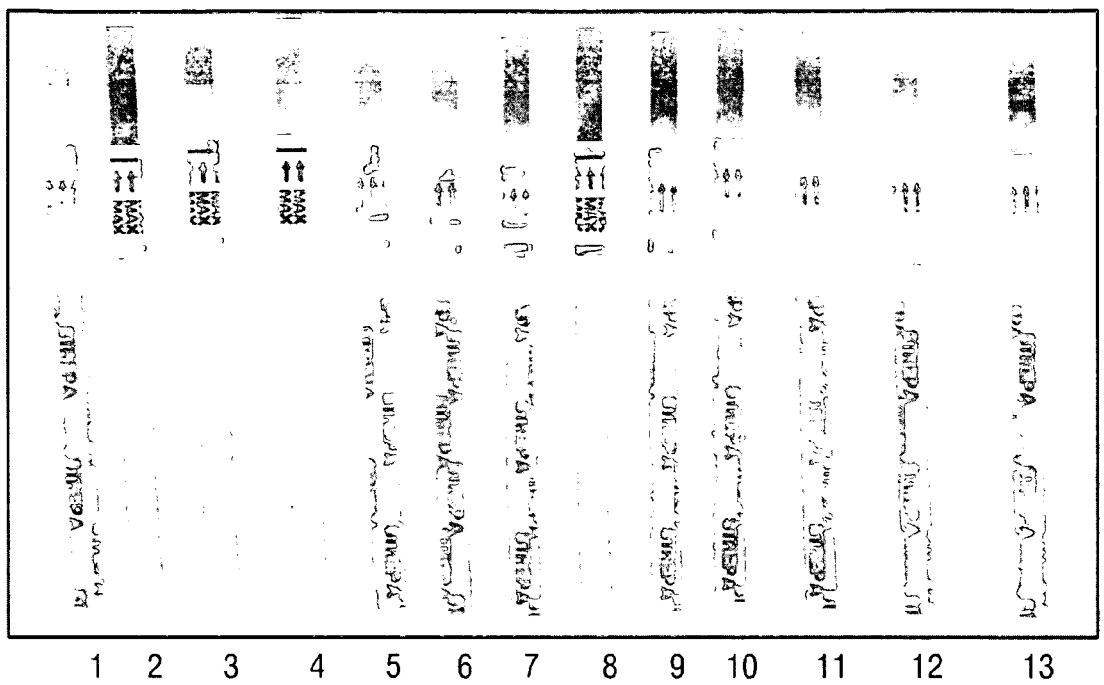
FIG. 9 shows test strips containing PAG-55 antibodies exposed to clotted blood samples.

To test the accuracy of using non-centrifuged whole blood samples in which the serum is extruded from clotted blood, the whole blood samples in the serum separator tubes were maintained at room temperature, without centrifugation, for a minimum of 20 minutes to allow clot formation. After the clot formed and retracted (the serum has been extruded or squeezed out of the clot by the contracting action of fibrin, this can be confirmed by visual observation), lateral flow test strips designed to detect pregnancy in bovines with anti-PAG-55 technology were placed in fluid communication (e.g. touching or in contact with the strip to facilitate uptake of the serum) with the serum layer in the serum separator tubes. The test strips were in contact with the serum that was extruded from the retracted clots; the serum being pulled into the strip by capillary action. The strips were allowed to develop for about 5 minutes. The results obtained showed distinct, reactive bands that were easy to interpret with the naked eye. FIG. 9 shows test strips exposed to clotted blood samples. Importantly, none of the samples using clotted blood samples exhibited red blood cell smears that interfered with reading the test lines. Instead, the clotted blood samples were easy to read, with the test line showing up in a distinct, clear fashion, as shown in the test strips in lanes 1-13 of FIG. 9. Additionally, there was no need for centrifugation of the SST tubes, the clotting process occurred while the tubes were maintained at room temperature in a tube rack, or other suitable means of level support. It should be noted that any suitable time may be used to allow clotting of the whole blood sample. Various factors may affect the time for clotting, such as temperature, humidity, and altitude.

For FIGS. 9 and 10, lanes 1-13 correspond to the following cow samples: lane 1=sample 3055; lane 2=sample 2999; lane 3=sample 2929; lane 4=2928; lane 5=2923; lane 6=2901; lane 7=2856; lane 8=2833; lane 9=2727; lane 10=2539; lane 11=2081; lane 12=1560; lane 13=683. Each strip was incubated with a 400 µl sample of blood (either clotted blood for FIG. 1, or non-clotted whole blood for FIG. 2).

While the methods and kits of this invention have been described in terms of preferred embodiments, it will be apparent to those of skill in the art that variations may be applied to the methods and kits described herein and in the steps or in the sequence of steps of the method described herein without departing from the inventive concept of the invention. More specifically, it will be apparent that certain agents which are both chemically and physiologically related may be substituted for the agents described herein while the same or similar results would be achieved. All such similar substitutes and modifications apparent to those skilled in the art are deemed to be within the scope and concept of the invention as defined by the appended claims.

REFERENCES

The following references, to the extent that they provide exemplary procedural or other details supplementary to those set forth herein, are specifically incorporated herein by reference:

U.S. Pat. No. 3,817,837
U.S. Pat. No. 3,850,752
U.S. Pat. No. 3,939,350
U.S. Pat. No. 3,996,345
U.S. Pat. No. 4,196,265
U.S. Pat. No. 4,275,149
U.S. Pat. No. 4,277,437
U.S. Pat. No. 4,366,241
U.S. Pat. No. 4,367,110
U.S. Pat. No. 4,452,901
U.S. Pat. No. 4,668,621
U.S. Pat. No. 4,683,195
U.S. Pat. No. 4,683,202
U.S. Pat. No. 4,800,159
U.S. Pat. No. 4,883,750
U.S. Pat. No. 5,279,721
U.S. Pat. No. 5,840,873
U.S. Pat. No. 5,843,640
U.S. Pat. No. 5,843,650
U.S. Pat. No. 5,843,651
U.S. Pat. No. 5,843,663
U.S. Pat. No. 5,846,708
U.S. Pat. No. 5,846,709
U.S. Pat. No. 5,846,717
U.S. Pat. No. 5,846,726
U.S. Pat. No. 5,846,729
U.S. Pat. No. 5,846,783
U.S. Pat. No. 5,849,481
U.S. Pat. No. 5,849,486
U.S. Pat. No. 5,849,487

U.S. Pat. No. 5,849,497
U.S. Pat. No. 5,849,546
U.S. Pat. No. 5,849,547
U.S. Pat. No. 5,851,772
U.S. Pat. No. 5,853,990
U.S. Pat. No. 5,853,992
U.S. Pat. No. 5,853,993
U.S. Pat. No. 5,856,092
U.S. Pat. No. 5,858,652
U.S. Pat. No. 5,861,244
U.S. Pat. No. 5,863,732
U.S. Pat. No. 5,863,753
U.S. Pat. No. 5,866,331
U.S. Pat. No. 5,866,366
U.S. Pat. No. 5,882,864
U.S. Pat. No. 5,900,481
U.S. Pat. No. 5,905,024
U.S. Pat. No. 5,910,407
U.S. Pat. No. 5,912,124
U.S. Pat. No. 5,912,145
U.S. Pat. No. 5,912,148
U.S. Pat. No. 5,916,776
U.S. Pat. No. 5,916,779
U.S. Pat. No. 5,919,626
U.S. Pat. No. 5,919,630
U.S. Pat. No. 5,922,574
U.S. Pat. No. 5,925,517
U.S. Pat. No. 5,928,862
U.S. Pat. No. 5,928,869
U.S. Pat. No. 5,928,905
U.S. Pat. No. 5,928,906
U.S. Pat. No. 5,929,227
U.S. Pat. No. 5,932,413
U.S. Pat. No. 5,932,451
U.S. Pat. No. 5,935,791
U.S. Pat. No. 5,935,825
U.S. Pat. No. 5,939,291
U.S. Pat. No. 5,942,391
U.S. Pat. No. 6,656,744
U.S. application Ser. No. 09/273,164
Amoroso, In: *Marshall's Physiology of Reproduction*, Parkes (Ed.), Little Brown and Co., Boston, 2:127-311, 952, 1952.
Ausubel et al. In: *Short Protocols in Molecular Biology*, John Wiley & Sons, 5$^{th}$ Ed., 2002.
Ayalon, N J, *J. Reprod. Fert.* 54:483-493, 1978.
Beal et al., *J. Anim. Sci.*, 70:924-929, 1992.
Bellus, *J. Macromol. Sci. Pure Appl. Chem.*, A31(1): 1355-1376, 1994.
Butler et al., *Biol. Reprod.*, 26:925-933, 1982.
Butler, W. R., *J. Dairy Sci.* 81:2533-2539, 1998.
Cameron and Malmo, *Austr. Vet. J.*, 70:109-111, 1993.
Campbell et al., *J. Mol. Biol.*, 180:1-19, 1984.
Capaldi et al., *Biochem. Biophys. Res. Comm.*, 76:425, 1977.
Chandrasekaran et al, *Indian Veterinary Journal*, 67:87-87, 1990.
Crowther, In: *Methods in Molecular Biology*, Vol. 42, Humana Press; New Jersey, 1995.
Engvall and Perlmann, *Immunochem.*, 8:871-873, 1971.
Engvall, *Lancet*, 2(8000):1410, 1976.
Engvall, *Med Biol.*, 55(4):193-200, 1977.
Engvall, *Methods Enzymol*, 70(A):419-39, 1980.
European App. 329 822.
European App. 320 308.
Fricke, P. M., *J. Dairy Sci.*, 85(8):1918-1926, 2002.
Frohman, In: *PCR Protocols: A Guide To Methods And Applications*, Academic Press, N.Y., 1990.
GB App. 2 202 328
Gefter et al., *Somatic Cell Genet.*, 3:231-236, 1977.
Goding, In: *Monoclonal Antibodies: Principles and Practice*, 2d ed., Academic Press, Orlando, Fla., pp 60-61, 71-74, 1986.
Green, Jonathan A. et al., *Theriogenology*, 63:1481-1503, 2005.
Gripenberg et al., *Scand J Immunol.*, 7(2):151-7, 1978.
Haig, *Rev. Biol.*, 68:495-532, 1993.
Harlow and Lane, In: *Antibodies, a Laboratory Manual*, Cold Spring Harbor Laboratory, pp 139-281, 1988.
Hatzidakis et al., *J. Reprod. Fertil.*, 98:235-240, 1993.
Holdsworth et al., *J. Endocrin.*, 95:7-12, 1982.
Huang et al., *J. Biol. Chem.*, 254:11405-11417, 1979.
Humblot et al., *Theriogenol.*, 30:257-268, 1988.
Innis et al. *Proc. Natl. Acad. Sci. USA*, 85(24), 9436-9440, 1988.
Kiracofe et al., *J. Anim. Sci.*, 71:2199-2205, 1993.
Kohler and Milstein, *Eur. J. Immunol.*, 6:511-519, 1976.
Kohler and Milstein, *Nature*, 256:495-497, 1975.
Kwoh et al., *Proc. Nat. Acad. Sci. USA*, 86: 1173, 1989.
Lu et al., *J. Immunoassay*, 18(2):149-163, 1997.
Markusfeld et al., *Br. Vet. J.*, 146: 504-508, 1990.
Mialon et al., *Reprod. Nutr. Dev.*, 33:269-282, 1993.
Mialon et al., *Reprod. Nutr. Dev.*, 34:65-72, 1994.
Nakamura et al., In: *Handbook of Experimental Inmunology* (4$^{th}$ Ed.), Weir et al. (Eds.), Blackwell Scientific Publ., Oxford, 1:27, 1987.
Ohara et al., *Proc. Natl. Acad. Sci.* USA, 86:5673-5677, 1989.
Oltenacu et al., *J. Dairy Sci.*, 73:2826-2831, 1990.
PCT App. PCT/US87/00880.
PCT App. PCT/US89/01025.
PCT App. PCT/US90/07641.
PCT App. WO 88/10315.
PCT App. WO 89/06700.
PCT App. WO 90/07641.
Roberts et al., *Biol. Reprod.*, 54:294-302, 1996.
Sambrook et al., In: *Molecular Cloning, A Laboratory Manual*, Cold Spring Harbor Laboratory Press, 2nd Ed., 1989.
Sambrook et al., In: *Molecular Cloning, A Laboratory Manual*, Cold Spring Harbor Laboratory Press, 3$^{rd}$ Ed., 2001.
Santos, J E P et al., *Journal of Dairy Science*, vol. 85 Supplement 1, pp. 265, 2002.
Sarngadharan et al., *Princess Takamatsu Symp.*, 15:301-8, 1984.
Sasser et al., *Biol. Reprod.* 35:936-942, 1986.
Stanley et al., *Veterinarian Record*, 664-667, 1986.
Stefanakis et al., *Bull. Hellenic Vet. Med. Soc.*, 45:37-43, 1994.
Streenan and Diskin, In: *Embryonic Mortality in Farm Animals*, Sreenan and Diskin (Eds.), Martinus Nijhoff Publishers, 1-11, 1986.
Vienravi et al., *J. Med. Assoc. Thai.*, 77(3): 138-47, 1994.
Walker et al., *Proc. Natl. Acad. Sci. USA*, 89:392-396 1992.
Warnick et al., *Theriogenol.*, 44:811-825, 1995.
Wiebold, J L, *J. Reprod. Fert.* 84:393-399, 1988.
Xie et al., *Biol. Reprod.*, 51:1145-1153, 1994.
Xie et al., *Biol. Reprod.*, 54: 122-129, 1996.
Xie et al., *Biol. Reprod.*, 57:1384-1393, 1997a.
Xie et al., *Gene*, 159:193-197, 1995.
Xie et al., *Proc. Natl. Acad. Sci. USA*, 94:12809-12816, 1997b.
Xie et al., *Proc. Natl. Acad. Sci. USA*, 88:10247-10251, 1991.
Zoli et al., *Biol. Reprod.*, 45:1-10, 1991.
Zoli et al., *Biol. Reprod.*, 46:623-629, 1992b.
Zoli et al., *Biol. Reprod.*, 46:83-92, 1992a.

The invention claimed is:

1. A method for detecting pregnancy in a cow comprising:
   (a) obtaining a sample from a first cow;
   (b) measuring a pregnancy-associated glycoprotein (PAG) level in said sample using an antigen-binding agent that recognizes the proteins of an acidic protein fraction of day 55 bovine placental tissue, wherein said PAG level comprises PAG-4, PAG-6, PAG-9, PAG-16, PAG-18, PAG-19 and Mon PAG, and wherein said antigen-binding agent comprises an antibody or an antigen-binding fragment of an antibody; and
   (c) comparing said PAG level with a control PAG level, wherein said control PAG level is or was measured using a non-pregnant cow;
wherein an elevation in said PAG level in comparison to the control PAG level indicates that said first cow is pregnant.

2. The method of claim 1, further comprising measuring the level of progesterone in said sample; wherein an elevated level of progesterone in said sample compared to the progesterone level in a non-pregnant cow further indicates that said first cow is pregnant.

3. The method of claim 1 or 2, wherein said sample is saliva, serum, plasma, whole blood, milk or urine.

4. The method of claim 3, wherein the sample is serum, plasma, or whole blood.

5. The method of claim 4, wherein the sample is whole blood and wherein the method further comprises:
   (i) allowing the whole blood to clot in the presence of a clot activator;
   (ii) allowing serum to extrude from the clotted whole blood without centrifugation;
   (iii) placing the extruded serum in liquid communication with detection means comprising said antigen-binding reagent; and
   (iv) determining said PAG level in the serum by reading the detection means.

6. The method of claim 5, wherein the clot activator is selected from the group consisting of thrombin, phospholipids, kaolin, micronized silica, and calcium.

7. The method of claim 1 or 2, wherein said sample is obtained from said first cow at any day from about day 15 to about day 30 post-insemination of said first cow.

8. The method of claim 1, wherein the first cow is a beef or dairy cow.

9. The method of claim 1, wherein said antigen-binding agent comprises polyclonal antisera or polyclonal antibodies.

10. The method of claim 1, wherein the antigen-binding agent comprises a mixture of monoclonal antibodies specific for PAG-4, PAG-6, PAG-9, PAG-16, PAG-18, PAG-19, and Mon PAG.

11. The method of claim 1, wherein said measuring step (b) comprises using ELISA, RIA, lateral flow technology based test strips, or Western blot.

12. The method of claim 9, wherein said antigen-binding agent comprises polyclonal antibodies that were raised against an acidic protein fraction of day 55 bovine placental tissue.

13. The method of claim 1 or 12, wherein the sample is serum, and wherein said PAG level is greater than 0.0 ng/ml.

14. The method of claim 13, wherein said PAG level is from about 1.0 ng/ml to about 5 ng/ml.

15. The method of claim 13, wherein said PAG level is about 2.0 ng/ml to about 3.0 ng/ml.

16. The method of claim 2, wherein measuring the progesterone level comprises immunologic detection.

17. The method of claim 2, wherein the sample is serum, and wherein the elevated level of progesterone is above about 2 ng/ml.

18. The method of claim 17, wherein the elevated level of progesterone is about 3 ng/ml.

19. The method of claim 2, wherein measuring the progesterone level comprises measuring progesterone biosynthesis pathway enzyme levels by immunologic detection or enzyme activity measurement.

20. The method of claim 2, wherein said sample is serum and is obtained from about days 20-30 post-insemination of the first cow, and the PAG and progesterone levels in the serum are about 0.5 to about 30 ng/ml and about 2 to about 5 ng/ml, respectively.

21. The method of claim 20, wherein said PAG level is about 1.0 ng/ml to about 5.0 ng/ml.

22. The method of claim 20, wherein said PAG level is about 2.0 ng/ml to about 3.0 ng/ml.

23. The method of claim 2, wherein said sample is serum and is obtained from about days 20-30 post-insemination of the first cow, and the PAG and progesterone levels in the serum are both at least 2 ng/ml.

24. The method of claim 1 or 2, further comprising obtaining a positive control sample from a pregnant cow.

25. The method of claim 2, further comprising measuring the PAG and progesterone levels from a second sample from said first cow at a second point in time.

26. A method of making a breeding decision for a cow comprising:
   (a) obtaining a sample from a first cow, wherein said first cow is suspected of being pregnant;
   (b) measuring a pregnancy-associated glycoprotein (PAG) level in said sample using an antigen-binding agent that recognizes the proteins of an acidic protein fraction of day 55 bovine placental tissue, wherein said PAG level comprises PAG-4, PAG-6, PAG-9, PAG-16, PAG-18, PAG-19 and Mon PAG, and wherein said antigen-binding agent comprises an antibody or an antigen-binding fragment of an antibody;

(c) measuring the level of progesterone in said sample, and (d) comparing said PAG and progesterone levels with control PAG and progesterone levels, respectively, wherein said control PAG and progesterone levels are or were measured using a non-pregnant cow;

wherein:

(i) elevated PAG and progesterone levels indicate that said first cow is pregnant;

(ii) non-elevated PAG and progesterone levels indicate that said first cow is not pregnant and should receive follow-up hormone therapy for re-breeding;

(iii) an elevated PAG level and non-elevated progesterone level indicate that said first cow is not pregnant due to a nonviable embryo and should receive follow-up hormone therapy for re-breeding; or (iv) a non-elevated PAG level and elevated progesterone level indicate that said first cow is not pregnant and should receive follow-up hormone therapy for re-breeding.

27. The method of claim 26, wherein said hormone therapy under condition (ii) comprises injecting the first cow with gonadotropin-releasing hormone (GnRH), and about seven days later, injecting with prostaglandin $F_{2\alpha}$ (PGF), followed by re-insemination.

28. The method of claim 26, wherein said hormone therapy under condition (iii) comprises injecting the first cow with GnRH, and about seven days later, injecting with PGF, followed by re-insemination.

29. The method of claim 26, wherein said hormone therapy under condition (iv) comprises injecting the first cow with PGF, followed by re-insemination.

30. The method of any one of claims 27-29, wherein said hormone therapy further comprises administering an injection of GnRH about 48 hours after said PGF injection and before said re-insemination.

31. The method of any one of claims 27-29, wherein said PGF injection is administered at day 20 post-insemination and wherein said re-insemination is carried out at day 28 post-insemination.

32. The method of any one of claims 27-29, wherein said PGE injection is administered at day 26 post-insemination and wherein re-insemination is carried out at day 28 post insemination.

33. A method of making a breeding decision for a cow comprising:

(a) obtaining a sample from a first cow, wherein said first cow is suspected of being pregnant;

(b) measuring a pregnancy-associated glycoprotein (PAG) level in said sample using an antigen-binding agent that recognizes the proteins of an acidic protein fraction of day 55 bovine placental tissue, wherein said PAG level comprises PAG-4, PAG-6, PAG-9, PAG-16, PAG-18, PAG-19 and Mon PAG, and wherein said antigen-binding agent comprises an antibody or an antigen-binding fragment of an antibody; and (c) comparing said PAG level with a control PAG level, wherein said control PAG level is or was measured using a non-pregnant cow; wherein:

(i) an elevated PAG level indicates that said first cow is pregnant; or (ii) a non-elevated PAG level indicates that said first cow is not pregnant and should receive appropriate hormone therapy for re-breeding.

34. The method of claim 33, wherein said hormone therapy under condition (ii) comprises injecting the first cow with gonadotropin-releasing hormone (GnRH), and about seven days later, injecting with prostaglandin $F_{2\alpha}$ (PGF), followed by re-insemination.

35. The method of claim 33, wherein said hormone therapy under condition (ii) comprises injecting the first cow with PGF, followed by re-insemination.

36. A method for detecting pregnancy in a cow comprising:

(a) obtaining a sample from a first cow;

(b) measuring the level of the proteins PAG-4, PAG-6, PAG-9, PAG-16, PAG-18, PAG-19 and Mon PAG in said sample; and (c) comparing the level measured in step (b) with a control level of said proteins, wherein said control level is or was measured using a non-pregnant cow;

wherein an elevation in the level measured in step (b) in comparison to the control level indicates that the first cow is pregnant.

37. The method of claim 36, wherein the sample is serum, plasma or whole blood.

38. The method of claim 37, wherein measuring step (b) is performed with polyclonal antibodies that were raised against an acidic protein fraction of day 55 bovine placental tissue.

* * * * *

UNITED STATES PATENT AND TRADEMARK OFFICE
CERTIFICATE OF CORRECTION

PATENT NO.         : 7,604,950 B2
APPLICATION NO.    : 11/587391
DATED              : October 20, 2009
INVENTOR(S)        : Mathialagan et al.

Page 1 of 1

It is certified that error appears in the above-identified patent and that said Letters Patent is hereby corrected as shown below:

Claim 32, Column 57, Line 44: delete "PGE" and insert --PGF--.

Signed and Sealed this

Fifteenth Day of December, 2009

David J. Kappos
*Director of the United States Patent and Trademark Office*